United States Patent
Higami et al.

(10) Patent No.: US 7,906,608 B2
(45) Date of Patent: Mar. 15, 2011

(54) NITROGENATED AROMATIC COMPOUND, PROCESS FOR PRODUCTION OF THE SAME, POLYMER, AND PROTON CONDUCTIVE MEMBRANE

(75) Inventors: Makoto Higami, Chuo-ku (JP); Igor Rozhanskii, Chuo-ku (JP); Yoshitaka Yamakawa, Chuo-ku (JP)

(73) Assignee: JSR Corporation, Tokyo (JP)

( * ) Notice: Subject to any disclaimer, the term of this patent is extended or adjusted under 35 U.S.C. 154(b) by 83 days.

(21) Appl. No.: 11/995,793

(22) PCT Filed: Jun. 30, 2006

(86) PCT No.: PCT/JP2006/313154
§ 371 (c)(1),
(2), (4) Date: Jan. 15, 2008

(87) PCT Pub. No.: WO2007/010731
PCT Pub. Date: Jan. 25, 2007

(65) Prior Publication Data
US 2009/0149623 A1    Jun. 11, 2009

(30) Foreign Application Priority Data

Jul. 15, 2005  (JP) .................................. 2005-207400
Jul. 15, 2005  (JP) .................................. 2005-207404

(51) Int. Cl.
*C08G 8/02* (2006.01)
(52) U.S. Cl. ...................... 528/125; 548/343.5; 548/170
(58) Field of Classification Search .................. 528/125; 548/343.5, 170
See application file for complete search history.

(56) References Cited

U.S. PATENT DOCUMENTS 5,028,717 A   7/1991  Gehring et al.
(Continued)

FOREIGN PATENT DOCUMENTS

CA   2 615 492 A1   1/2007
(Continued)

OTHER PUBLICATIONS

Paul D. Bloom, et al., "Novel Poly(p-phenylene)s via Nucleophilic Aromatic Substitution of Poly(4'-fluoro-2,5-benzophenone)", Macromolecules, vol. 38, No. 6, American Chemical Society, XP-002540027, Feb. 2005, pp. 2159-2166.

(Continued)

*Primary Examiner* — Randy Gulakowski
*Assistant Examiner* — Shane Fang
(74) *Attorney, Agent, or Firm* — Oblon, Spivak, McClelland, Maier & Neustadt, L.L.P.

(57) ABSTRACT

A nitrogen-containing aromatic compound is represented by Formula (1). A polymer is obtained by polymerizing the compound.

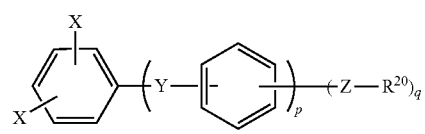

(1)

wherein X is an atom or a group selected from halogen atoms other than fluorine and $-OSO_2Rb$ (wherein Rb is an alkyl group, a fluorine-substituted alkyl group or an aryl group); Y is at least one structure selected from the group consisting of $-CO-$, $-SO_2-$, $-SO-$, $-CONH-$, $-COO-$, $-(CF_2)_l-$ (wherein l is an integer of 1 to 10) and $-C(CF_3)_2-$; Z is at least one structure selected from the group consisting of a direct bond, $-O-$ and $-S-$; $R^{20}$ is a nitrogen-containing heterocyclic group; q is an integer of 1 to 5; and p is an integer of 0 to 4.

16 Claims, 1 Drawing Sheet

U.S. PATENT DOCUMENTS

| | | |
|---|---|---|
| 5,189,040 A | 2/1993 | Ohsumi et al. |
| 2001/0044445 A1 | 11/2001 | Bamaung et al. |
| 2004/0044166 A1* | 3/2004 | Rozhanskii et al. ............ 528/86 |
| 2004/0166435 A1* | 8/2004 | Lee et al. ................... 430/270.1 |
| 2005/0072971 A1 | 4/2005 | Marrocco, III et al. |

FOREIGN PATENT DOCUMENTS

| | | |
|---|---|---|
| DE | 31 39 457 A1 | 4/1983 |
| JP | 52 31067 | 3/1977 |
| JP | 2004 137444 | 5/2004 |
| JP | 2004-345997 | 12/2004 |
| JP | 2004-346163 | 12/2004 |
| JP | 2004 346164 | 12/2004 |
| JP | 2005 82757 | 3/2005 |
| JP | 2005 126391 | 5/2005 |
| WO | 87/04321 | 7/1987 |
| WO | WO 99/62885 | 12/1999 |
| WO | WO 02/062804 A1 | 8/2002 |

OTHER PUBLICATIONS

Paul D. Bloom, et al., Nucleophilic aromatic substitution of Poly (4'-fluoro-2,5-benzophenone), Polymeric Materials: Science & Engineering, vol. 84, XP009121076, 2001, pp. 562-563.

Database WPI Section Ch, Week 200503 Thomson Scientific, London, GB; Class A85, AN 2005-024084, XP002584526 (Corresponds to JP 2004-346163 A filed on Jun. 3, 2008).

Chinese Office Action issued Sep. 30, 2010.

* cited by examiner

NITROGENATED AROMATIC COMPOUND, PROCESS FOR PRODUCTION OF THE SAME, POLYMER, AND PROTON CONDUCTIVE MEMBRANE

FIELD OF THE INVENTION

The present invention relates to polymers having improved heat stability, more particularly to polymers that have high stability of sulfonic acid groups at high temperatures and can give a proton conductive membrane that shows high durability in power generation of a fuel cell at high temperatures. The invention also relates to monomer compounds for producing the polymers.

BACKGROUND OF THE INVENTION

Fuel cells are an electricity generation system that produces electricity directly by electrochemical reaction of atmospheric oxygen with hydrogen gas or hydrogen obtained by reforming various hydrocarbon fuels (such as natural gases and methane). They provide highly efficient and direct conversion of the fuel's chemical energy to electrical energy. This fact and their non-polluting properties make the generation system more attractive.

The fuel cells are made up of a proton conductive electrolyte membrane (proton conductive membrane) sandwiched between a pair of electrode membranes (fuel electrode and air electrode) on which a catalyst is supported. The catalyst on the fuel electrode separates hydrogen into protons and electrons. The protons pass through the proton conductive membrane and react with oxygen at the air electrode, producing water.

The fuel cells in recent years are required to show higher generating performance. For the fuel cells to generate more electricity, they should be operated at high temperatures. The proton conductive membranes used in the fuel cells are thus required to exhibit high proton conductivity in a variety of environments, in particular at high temperatures.

Polymers having sulfonic acid groups are usually used as proton conductive membranes. The present applicant has proposed proton conductive membranes with high proton conductivity comprising specific polymers having sulfonic acid groups in JP-A-2004-345997 (Patent Document 1), JP-A-2004-346163 (Patent Document 2) and JP-A-2004-346164 (Patent Document 3).
Patent Document 1: JP-A-2004-345997
Patent Document 2: JP-A-2004-346163
Patent Document 3: JP-A-2004-346164

DISCLOSURE OF THE INVENTION

Problems to be Solved by the Invention

However, the use of the conventional proton conductive membranes of the polymers having sulfonic acid groups at high temperatures often results in reversible detachment of the sulfonic acid groups and crosslinking reaction involving the sulfonic acid groups. Thereby, proton conductivity was reduced and the membrane was embritted. Moreover, the lowering of generation output of the fuel cell was lowered and generation failure by breakage of the membrane was caused. The probability of these problems is currently minimized by limiting a maximum temperature at which the fuel cells are operated. The generation output is thus limited.

There has been a demand for polymers that are capable of providing proton conductive membranes having proton conductivity and excellent heat resistance. For this demand, development has been demanded of monomers that are materials for such polymers.

Means for Solving the Problems

The present inventors have studied diligently to solve the aforesaid problems. They have then found that by introducing nitrogen-containing heterocyclic aromatic groups into a polymer having sulfonic acid groups, the sulfonic acid groups show improved stability at high temperatures and the above problems are solved. The inventors have found specific compounds as material monomers for the polymers, and the compounds have been found to possess high copolymerizability with other monomers and to ensure high proton conductivity, thus solving the conventional problems. The present invention has been completed based on the findings.

The present invention is directed to the following.

[1-1] A nitrogen-containing aromatic compound represented by Formula (1):

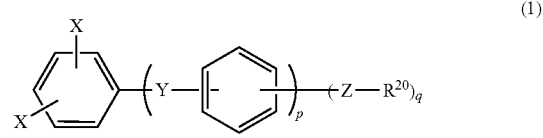

wherein X is an atom or a group selected from halogen atoms other than fluorine and —$OSO_2Rb$ (wherein Rb is an alkyl group, a fluorine-substituted alkyl group or an aryl group); Y is at least one structure selected from the group consisting of —CO—, —$SO_2$—, —SO—, —CONH—, —COO—, —$(CF_2)_l$— (wherein l is an integer of 1 to 10) and —$C(CF_3)_2$—; Z is at least one structure selected from the group consisting of a direct bond, —O— and —S—; $R^{20}$ is a nitrogen-containing heterocyclic group; q is an integer of 1 to 5; and p is an integer of 0 to 4.

[1-2] The nitrogen-containing aromatic compound described in [1-1], wherein the nitrogen-containing heterocyclic group is at least one group derived from a compound selected from the group consisting of nitrogen-containing heterocyclic compounds and derivatives thereof selected from pyrrole, thiazole, isothiazole, oxazole, isoxazole, pyridine, imidazole, imidazoline, pyrazole, 1,3,5-triazine, pyrimidine, pyridazine, pyrazine, indole, quinoline, isoquinoline, purine, benzimidazole, benzoxazole, benzthiazole, tetrazole, tetrazine, triazole, carbazole, acridine, quinoxaline, quinazoline and derivatives of these compounds.

[1-3] A process for producing the nitrogen-containing aromatic compound described in [1-1], the process comprising reacting a nitrogen-containing heterocyclic compound with a compound represented by Formula (2):

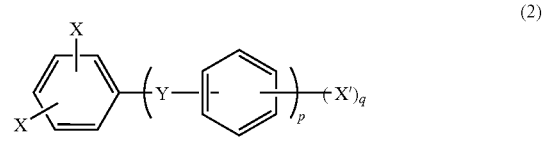

wherein X is an atom or a group selected from halogen atoms other than fluorine and —$OSO_2Rb$ (wherein Rb is an alkyl group, a fluorine-substituted alkyl group or an aryl group); Y is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; q is an integer of 1 to 5; p is an integer of 0 to 4; and X' is a halogen atom.

[2-1] A polymer comprising a main chain comprising a polyphenylene structure, and a structure comprising a side chain having a sulfonic acid group and a side chain having a nitrogen-containing heterocyclic group.

[2-2] The polymer described in [2-1], wherein the side chain having a nitrogen-containing heterocyclic group is represented by Formula (D):

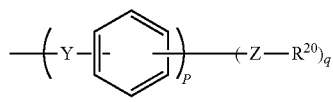

(D)

wherein Z is at least one structure selected from the group consisting of a direct bond, —O— and —S—; Y is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; R$^{20}$ is a nitrogen-containing heterocyclic group; q is an integer of 1 to 5; and p is an integer of 0 to 4.

[2-3] The polymer described in [2-1] or [2-2], wherein the nitrogen-containing heterocyclic group is at least one group derived from a compound selected from the group consisting of nitrogen-containing heterocyclic compounds and derivatives thereof selected from pyrrole, thiazole, isothiazole, oxazole, isoxazole, pyridine, imidazole, imidazoline, pyrazole, 1,3,5-triazine, pyrimidine, pyridazine, pyrazine, indole, quinoline, isoquinoline, purine, benzimidazole, benzoxazole, benzthiazole, tetrazole, tetrazine, triazole, carbazole, acridine, quinoxaline, quinazoline and derivatives of these compounds.

[2-4] The polymer described in [2-1], wherein the side chain having a sulfonic acid group is represented by Formula (E):

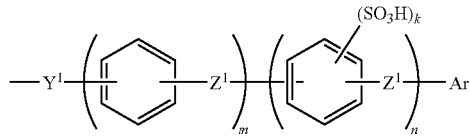

(E)

integer of 1 to 10), —C(CH$_3$)$_2$—, —O— and —S—; Ar is an aromatic group having a substituent represented by —SO$_3$H, —O(CH$_2$)$_h$SO$_3$H or —O(CF$_2$)$_h$SO$_3$H (wherein h is an integer of 1 to 12); m is an integer of 0 to 10; n is an integer of 0 to 10; and k is an integer of 1 to 4.

[2-5] The polymer described in [2-1], wherein the polymer includes a repeating structural unit represented by Formula (C) and a repeating unit represented by Formula (A):

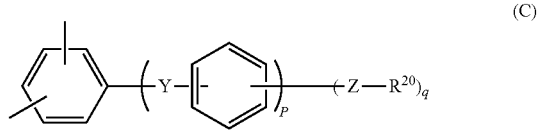

(C)

wherein Z is at least one structure selected from the group consisting of a direct bond, —O— and —S—; Y is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; R$^{20}$ is a nitrogen-containing heterocyclic group; q is an integer of 1 to 5; and p is an integer of 0 to 4;

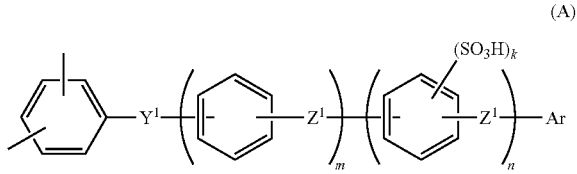

(A)

wherein Y$^1$ is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; Z$^1$ is at least one structure selected from the group consisting of a direct bond, —(CH$_2$)$_l$— (wherein l is an integer of 1 to 10), —C(CH$_3$)$_2$—, —O— and —S—; Ar is an aromatic group having a substituent represented by —SO$_3$H, —O(CH$_2$)$_h$SO$_3$H or —O(CF$_2$)$_h$SO$_3$H (wherein h is an integer of 1 to 12); m is an integer of 0 to 10; n is an integer of 0 to 10; and k is an integer of 1 to 4.

[2-6] The polymer described in [2-5], wherein the polymer further includes a structure represented by Formula (B):

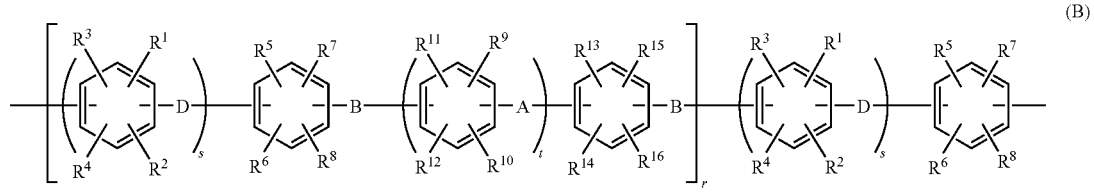

(B)

wherein Y$^1$ is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; Z$^1$ is at least one structure selected from the group consisting of a direct bond, —(CH$_2$)$_l$— (wherein l is an wherein A and D are each at least one structure selected from the group consisting of a direct bond, —CO—, —SO$_2$—, —SO—, —CONH—, —COO—, —(CF$_2$)$_l$— (wherein l is an integer of 1 to 10), —(CH$_2$)$_l$— (wherein l is an integer of 1 to 10), —CR'$_2$— (wherein R' is an aliphatic hydrocarbon group, an aromatic hydrocarbon group or a halogenated hydrocarbon group), a cyclohexylidene group, a fluorenylidene group, —O— and —S—; Bs are each an oxygen atom or a sulfur atom; $R^1$ to $R^{16}$ are the same or different from one another and are each at least one atom or group selected from the group consisting of a hydrogen atom, a fluorine atom, alkyl groups, partially or completely halogenated alkyl groups, allyl groups, aryl groups, nitro group and nitrile group; s and t are each an integer of 0 to 4; and r is an integer of 0 or 1 or greater.

[2-7] A proton conductive membrane comprising the polymer described in any of [2-1] to [2-6].

ADVANTAGES OF THE INVENTION

According to the invention, nitrogen-containing heterocyclic aromatic groups are effectively introduced into polyarylenes with sulfonic acid groups that are used as proton conductive membranes.

According to the invention, nitrogen-containing heterocyclic aromatic groups are introduced into polymers that inherently have excellent hot water resistance, high sulfonic acid concentration and superior proton conductivity. The polymers obtained by the introduction can give proton conductive membranes that show high stability of the sulfonic acid at high temperatures while the proton conductivity is ensured. The polymers used as proton conductive membranes for fuel cells allow for power generation in a wide range of temperature and humidity, in particular at high temperatures. The output of electricity generation is thus improved. The sulfonic acid groups are highly stable even at high temperatures, and the fuel cells according to the present invention achieve a drastically increased cell life.

BEST MODE FOR CARRYING OUT THE INVENTION

Figure 1:
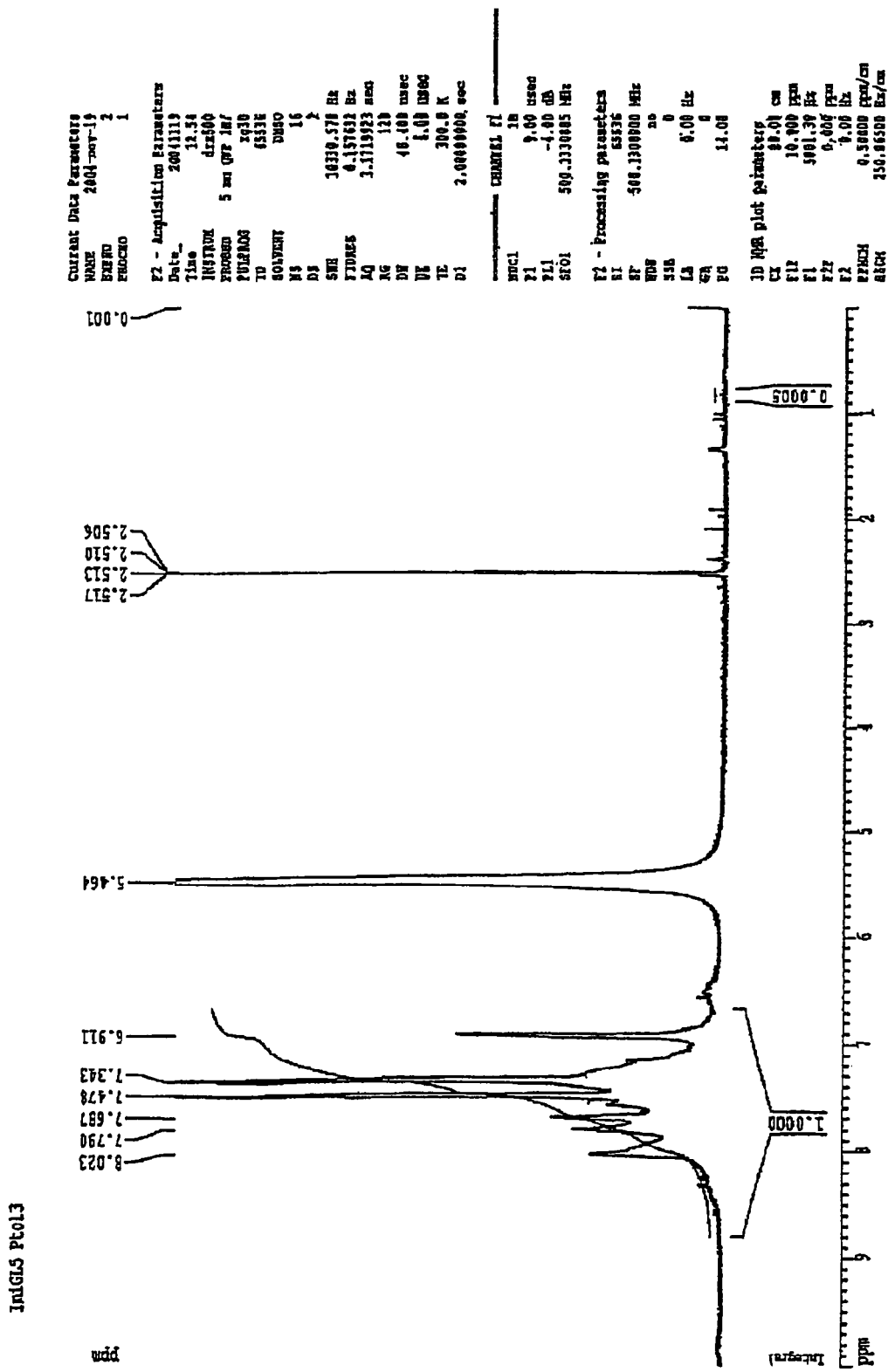
FIG. 1 shows a $^1$H-NMR spectrum of a compound obtained in Example 1.

Best modes for carrying out the present invention will be described below.

[Nitrogen-containing Aromatic Compounds]

The nitrogen-containing aromatic compounds of the present invention are represented by Formula (1):

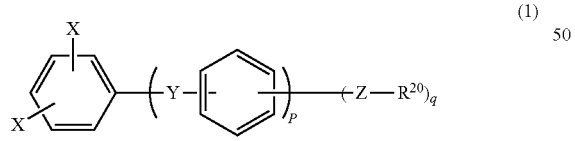

X is an atom or a group selected from halogen atoms other than fluorine and —OSO$_2$Rb (wherein Rb is an alkyl group, a fluorine-substituted alkyl group or an aryl group).

Y is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—, and is preferably —CO— or —SO$_2$—, and is more preferably —CO—. Z is at least one structure selected from the group consisting of a direct bond, —O— and —S—, and is preferably a direct bond or —O—.

$R^{20}$ is a nitrogen-containing heterocyclic group. Examples include groups derived from nitrogen-containing heterocyclic compounds and derivatives thereof by elimination of a hydrogen atom bonded to carbon or nitrogen. The nitrogen-containing heterocyclic compounds include pyrrole, thiazole, isothiazole, oxazole, isoxazole, pyridine, imidazole, imidazoline, pyrazole, 1,3,5-triazine, pyrimidine, pyridazine, pyrazine, indole, quinoline, isoquinoline, purine, benzimidazole, benzoxazole, benzthiazole, tetrazole, tetrazine, triazole, carbazole, acridine, quinoxaline and quinazoline.

The nitrogen-containing heterocyclic groups may have a substituent, with examples including alkyl groups such as methyl, ethyl and propyl; aryl groups such as phenyl, toluoyl and naphthyl; a cyano group; and a fluorine atom.

The letter q is an integer of 1 to 5, and is preferably 1 or 2.

The letter p is an integer of 0 to 4, and is preferably 0 or 1.

Specific examples of the nitrogen-containing aromatic compounds represented by Formula (1) include the following compounds.

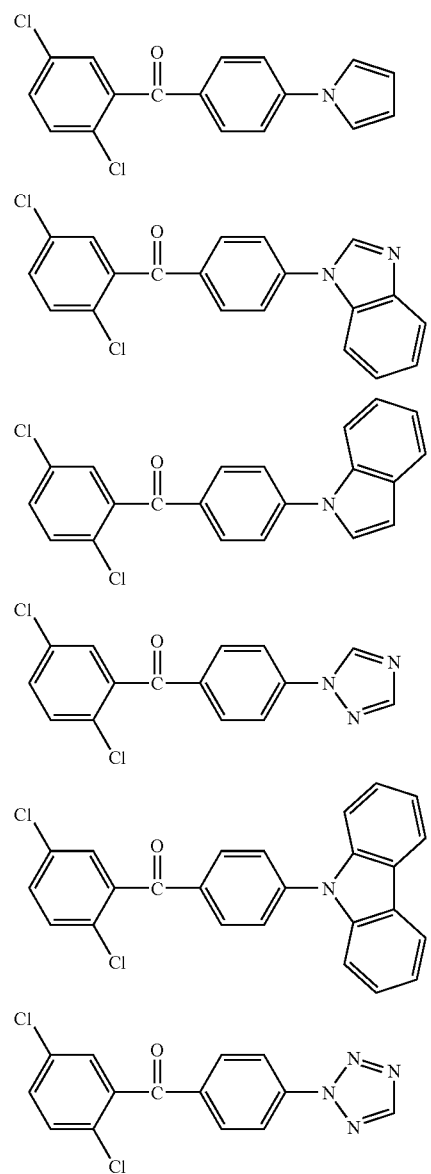

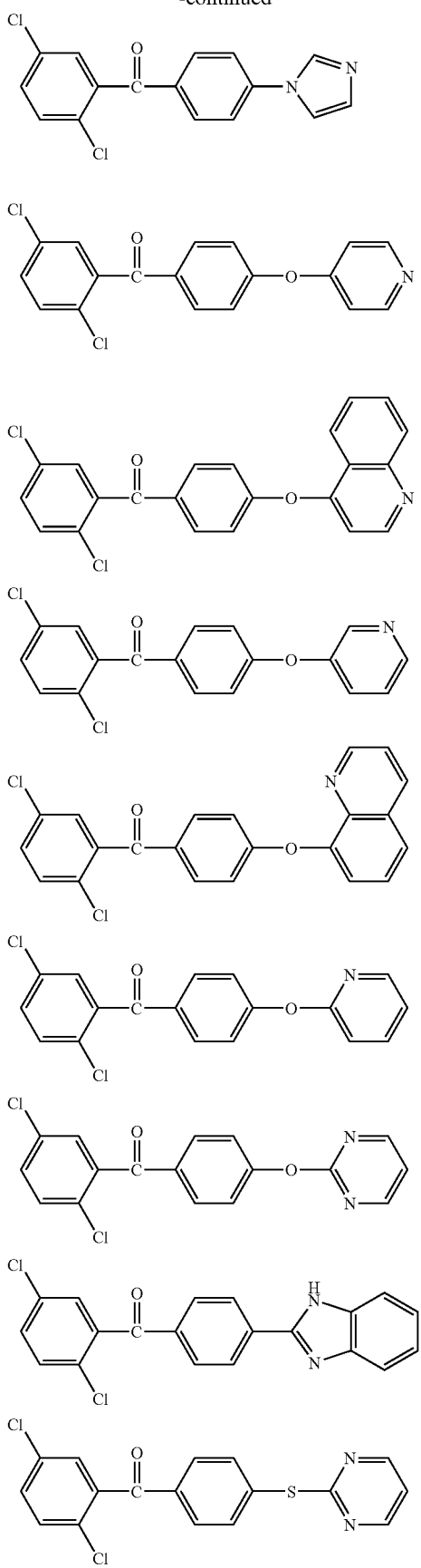
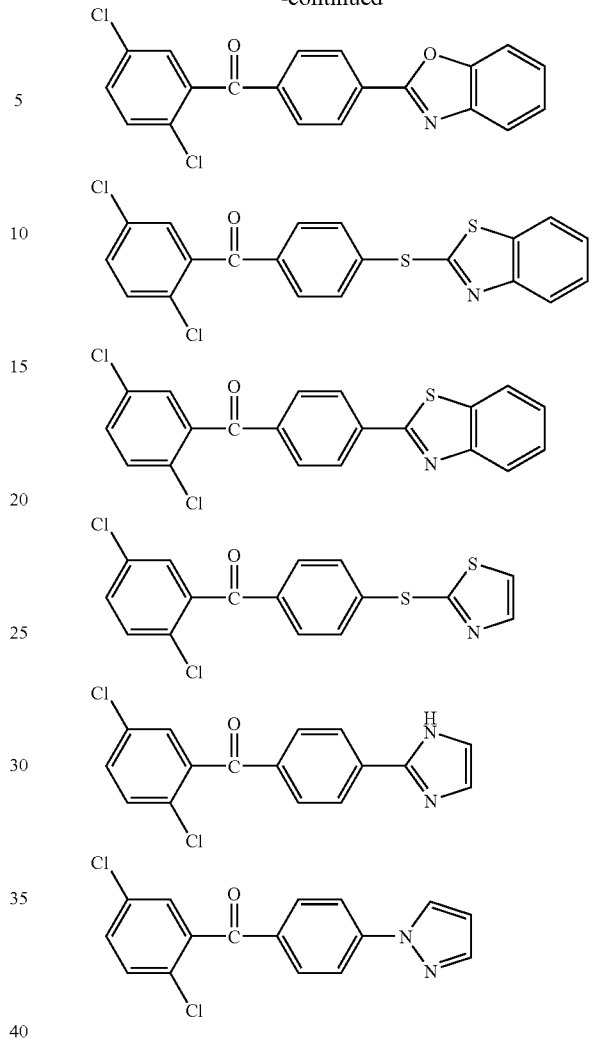

The invention may employ derivatives of the above compounds in which the chlorine atoms are replaced by bromine atoms, and isomers in which the chlorine atoms and bromine atoms are bonded at different positions. Derivatives of the above compounds in which the —CO— bond is replaced by —SO$_2$— bond are also employable.

The nitrogen-containing aromatic compounds of the invention may be synthesized by the following method as an example.

A compound represented by Formula (2) and a nitrogen-containing heterocyclic compound are subjected to nucleophilic substitution reaction.

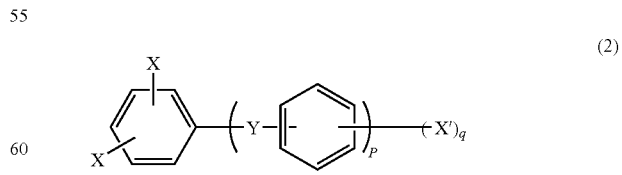

wherein X, Y, p and q are as described in Formula (1).

X' is a halogen atom, preferably a fluorine atom or a chlorine atom, more preferably a fluorine atom.

Specific examples of the compounds represented by Formula (2) include 2,4-dichloro-4'-fluorobenzophenone, 2,5- dichloro-4'-fluorobenzophenone, 2,6-dichloro-4'-fluorobenzophenone, 2,4-dichloro-2'-fluorobenzophenone, 2,5-dichloro-2'-fluorobenzophenone, 2,6-dichloro-2'-fluorobenzophenone, 2,4-dichlorophenyl-4'-fluorophenylsulfone, 2,5-dichlorophenyl-4'-fluorophenylsulfone, 2,6-dichlorophenyl-4'-fluorophenylsulfone, 2,4-dichlorophenyl-2'-fluorophenylsulfone, 2,4-dichlorophenyl-2'-fluorophenylsulfone and 2,4-dichlorophenyl-2'-fluorophenylsulfone.

Of these compounds, 2,5-dichloro-4'-fluorobenzophenone is preferable.

The nitrogen-containing heterocyclic compound has active hydrogen. The active hydrogen undergoes the substitution reaction with the group X' of the compound represented by Formula (2).

Examples of the nitrogen-containing heterocyclic compounds with active hydrogen include pyrrole, thiazole, isothiazole, oxazole, isoxazole, pyridine, imidazole, imidazoline, pyrazole, 1,3,5-triazine, pyrimidine, pyridazine, pyrazine, indole, quinoline, isoquinoline, purine, benzimidazole, benzoxazole, benzthiazole, tetrazole, tetrazine, triazole, carbazole, acridine, quinoxaline, quinazoline, 2-hydroxypyridine, 3-hydroxypyridine, 4-hydroxypyridine, 3-hydroxyquinoline, 8-hydroxyquinoline, 2-hydroxypyrimidine, 2-mercaptopyridine, 3-mercaptopyridine, 4-mercaptopyridine, 2-mercaptopyrimidine and 2-mercaptobenzthiazole.

When the heterocyclic compound has a hydroxyl group or a mercapto group, the hydrogen bonded to the oxygen atom or the sulfur atom is active hydrogen. In this case, the nitrogen-containing heterocyclic ring is introduced via the —O— bond or the —S— bond. The hydrogen atom bonded to the nitrogen atom of the nitrogen-containing heterocyclic ring, and the hydrogen atoms bonded to atoms other than the nitrogen in the heterocyclic ring are also active. In this case, the nitrogen-containing heterocyclic ring is introduced through a direct bond formed between the compound and the nitrogen-containing heterocyclic ring.

Of these compounds, pyrrole, imidazole, indole, carbazole, benzoxazole and benzimidazole are preferred.

The compound of Formula (2) and the nitrogen-containing heterocyclic compound with active hydrogen are preferably reacted in an organic solvent. Examples of the organic solvents include polar solvents such as N-methyl-2-pyrrolidone, N,N-dimethylacetamide, sulfolane, diphenyl sulfone and dimethyl sulfoxide. An alkali metal, an alkali metal hydride, an alkali metal hydroxide or an alkali metal carbonate may be used to accelerate the reaction. The compound of Formula (2) and the nitrogen-containing heterocyclic compound with active hydrogen may be used in equimolar amounts. Alternatively, the nitrogen-containing heterocyclic compound with active hydrogen may be used in excess. Specifically, the nitrogen-containing heterocyclic compound with active hydrogen is preferably used in a molar amount 1 to 3 times, particularly preferably 1 to 1.5 times that of the compound of Formula (2).

The reaction temperature is in the range of 0 to 300° C., preferably 10 to 200° C. The reaction time is in the range of 15 minutes to 100 hours, preferably 1 to 24 hours.

The reaction product is preferably purified, for example by recrystallization.

The nitrogen-containing aromatic compound may be used as a monomer for polymerization. Specifically, it is useful as a monomer for polyphenylenes, polyarylenes, polyethers, polyether ketones and polyether sulfones.

[Polymer]

The polymer according to the present invention comprises a main chain comprising a polyphenylene structure, and a structure comprising a side chain having a sulfonic acid group and a side chain having a nitrogen-containing heterocyclic group.

The polyphenylene structure of the main chain is represented by the following formula. The side chains are represented by substituent $R^2$ in the structure.

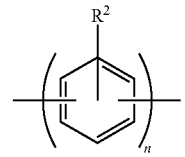

Side Chains

The side chain having a nitrogen-containing heterocyclic group is represented by Formula (D):

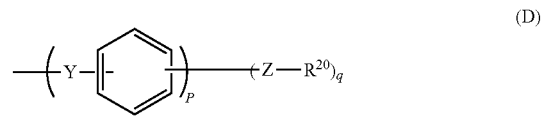

(D)

wherein Z, Y, $R^{20}$ and p are as described in Formula (1). Specifically, D is at least one structure selected from the group consisting of a direct bond, —O— and —S—; and Y is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—, and is preferably —CO—.

$R^{20}$ is a nitrogen-containing heterocyclic group. Examples include groups derived from nitrogen-containing heterocyclic compounds and derivatives thereof by elimination of a hydrogen atom bonded to carbon or nitrogen. The nitrogen-containing heterocyclic compounds include pyrrole, thiazole, isothiazole, oxazole, isoxazole, pyridine, imidazole, imidazoline, pyrazole, 1,3,5-triazine, pyrimidine, pyridazine, pyrazine, indole, quinoline, isoquinoline, purine, benzimidazole, benzoxazole, benzthiazole, tetrazole, tetrazine, triazole, carbazole, acridine, quinoxaline and quinazoline.

The nitrogen-containing heterocyclic groups may have a substituent, with examples including alkyl groups such as methyl, ethyl and propyl; aryl groups such as phenyl, toluoyl and naphthyl; a cyano group; and a fluorine atom.

The letter q is an integer of 1 to 5, and is preferably 1 or 2.
The letter p is an integer of 0 to 4, and is preferably 0 or 1.
The side chain having a sulfonic acid group is represented by Formula (E):

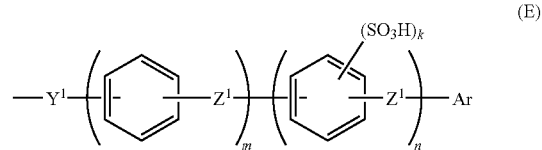

(E)

In Formula (E), $Y^1$ is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—, with —CO— and —SO$_2$— being preferable.

$Z^1$ is at least one structure selected from the group consisting of a direct bond, —(CH$_2$)$_l$— (wherein l is an integer of 1 to 10), —C(CH$_3$)$_2$—, —O— and —S—, with a direct bond and —O— being preferable.

Ar is an aromatic group having a substituent represented by —SO$_3$H, —O(CH$_2$)$_h$SO$_3$H or —O(CF$_2$)$_h$SO$_3$H (wherein h is an integer of 1 to 12). Examples of the aromatic groups include phenyl, naphthyl, anthryl and phenanthryl groups, with the phenyl and naphthyl groups being preferable. The aromatic group should have at least one substituent represented by —$SO_3H$, —$O(CH_2)_nSO_3H$ or —$O(CF_2)_nSO_3H$. In the case of the naphthyl group, it preferably has two or more such substituents.

The letter m is an integer of 0 to 10, preferably 0 to 2. The letter n is an integer of 0 to 10, preferably 0 to 2. The letter k is an integer of 1 to 4.

Preferable combinations of the values of m and n, and the structures of Y, Z and Ar include:
(1) Structures in which m=0, n=0, $Y^1$ is —CO—, and Ar is a phenyl group having a substituent —$SO_3H$;
(2) Structures in which m=1, n=0, $Y^1$ is —CO—, $Z^1$ is —O—, and Ar is a phenyl group having a substituent —$SO_3H$;
(3) Structures in which m=1, n=1, k=1, $Y^1$ is —CO—, $Z^1$ is —O—, and Ar is a phenyl group having a substituent —$SO_3H$;
(4) Structures in which m=1, n=0, $Y^1$ is —CO—, $Z^1$ is —O—, and Ar is a naphthyl group having two substituents —$SO_3H$; and
(5) Structures in which m=1, n=0, $Y^1$ is —CO—, $Z^1$ is —O—, and Ar is a phenyl group having a substituent —$O(CH_2)_4SO_3H$.

In the side chains (D) and (E), $Y^1$ and $Z^1$ may be the same or different.

Polymer

The polymer according to the present invention includes repeating units represented by Formula (C) and Formula (A):

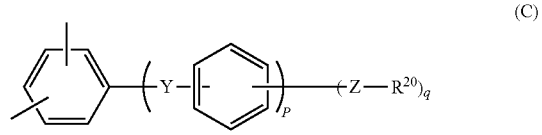

(C)

wherein Y, Z, $R^{20}$, q and p are as described in Formula (D);

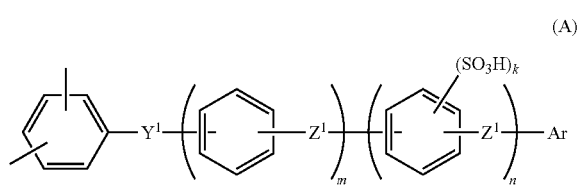

(A)

wherein $Y^1$, $Z^1$, Ar, m, n and k are as described in Formula (E). Preferably, the polymer further includes repeating units represented by Formula (B):

an integer of 1 to 10), —$CR'_2$— (wherein R' is an aliphatic hydrocarbon group, an aromatic hydrocarbon group or a halogenated hydrocarbon group), a cyclohexylidene group, a fluorenylidene group, —O— and —S—. Specific examples of the —$CR'_2$— include methyl, ethyl, propyl, isopropyl, butyl, isobutyl, t-butyl, propyl, octyl, decyl, octadecyl, phenyl and trifluoromethyl groups.

Of the structures, a direct bond, —CO—, —$SO_2$—, —$CR'_2$— (wherein R' is an aliphatic hydrocarbon group, an aromatic hydrocarbon group or a halogenated hydrocarbon group), a cyclohexylidene group, a fluorenylidene group and —O— are preferable.

Bs are each an oxygen atom or a sulfur atom, with the oxygen atom being preferable. $R^1$ to $R^{16}$ are the same or different from one another and are each at least one atom or group selected from the group consisting of a hydrogen atom, a fluorine atom, alkyl groups, partially or completely halogenated alkyl groups, allyl groups, aryl groups, nitro group and nitrile group.

Examples of the alkyl groups include methyl, ethyl, propyl, butyl, amyl, hexyl, cyclohexyl and octyl groups. Examples of the halogenated alkyl groups include trifluoromethyl, pentafluoroethyl, perfluoropropyl, perfluorobutyl, perfluoropentyl and perfluorohexyl groups. Examples of the allyl groups include propenyl group. Examples of the aryl groups include phenyl and pentafluorophenyl groups.

The letters s and t are each an integer of 0 to 4. The letter r is an integer of 0 or 1 or greater, generally up to 100, and is preferably in the range of 1 to 80. Preferred combinations of the values of s and t, and the structures of A, B, D and $R^1$ to $R^{16}$ include:

(1) Structures in which s=1, t=1, A is —$CR'_2$— (wherein R' is an aliphatic hydrocarbon group, an aromatic hydrocarbon group or a halogenated hydrocarbon group), a cyclohexylidene group or a fluorenylidene group, B is an oxygen atom, D is —CO— or —$SO_2$—, and $R^1$ to $R^{16}$ are hydrogen atoms or fluorine atoms;

(2) Structures in which s=1, t=0, B is an oxygen atom, D is —CO— or —$SO_2$—, and $R^1$ to $R^{16}$ are hydrogen atoms or fluorine atoms; and (3) Structures in which s=0, t=1, A is —$CR'_2$— (wherein R' is an aliphatic hydrocarbon group, an aromatic hydrocarbon group or a halogenated hydrocarbon group), a cyclohexylidene group or a fluorenylidene group, B is an oxygen atom, and $R^1$ to $R^{16}$ are hydrogen atoms, fluorine atoms or nitrile groups.

The polymer used in the invention includes the repeating units with a sulfonic acid group (sulfonic acid units) represented by Formula (A), the repeating units without a sulfonic acid group (hydrophobic units) represented by Formula (B), and the nitrogen-containing heterocyclic groups (nitrogen-containing heterocyclic aromatic units) represented by Formula (C). The polymer is represented by Formula (F):

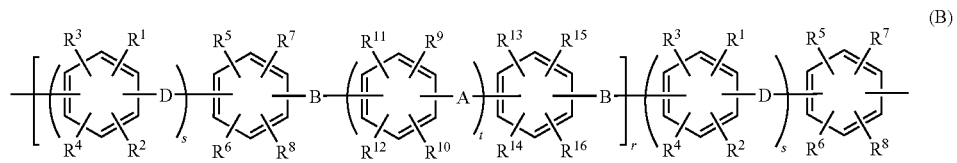

(B)

In Formula (B), A and D are each at least one structure selected from the group consisting of a direct bond, —CO—, —$SO_2$—, —SO—, —CONH—, —COO—, —$(CF_2)_l$— (wherein l is an integer of 1 to 10), —$(CH_2)_l$— (wherein l is

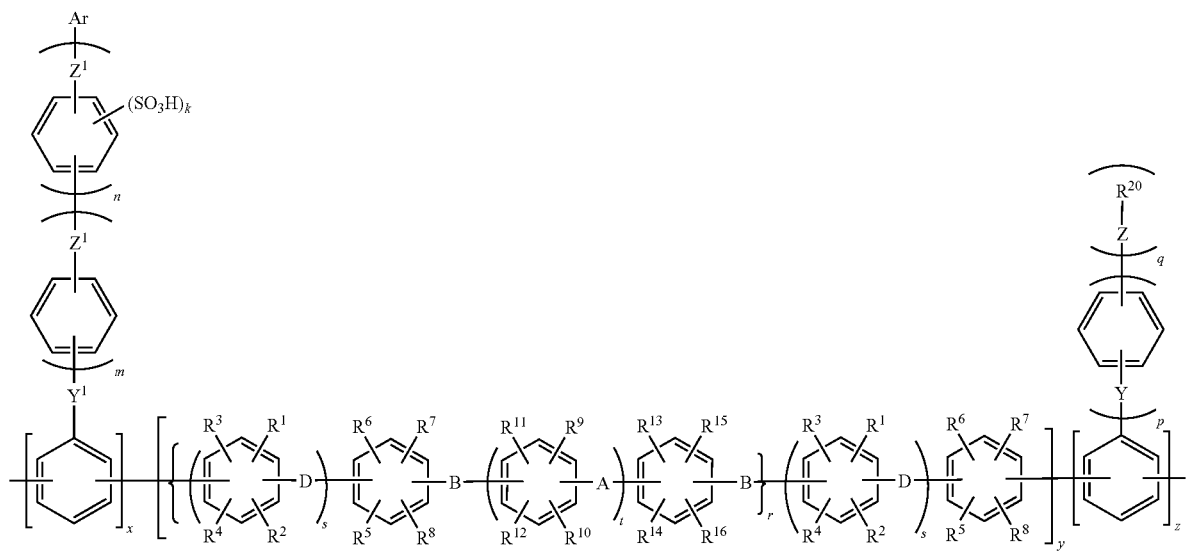

(F)

wherein A, B, D, Y, Z, $Y^1$, $Z^1$, Ar, k, m, n, p, q, r, s, t, $R^{20}$ and $R^1$ to $R^{16}$ are the same as A, B, D, Y, Z, $Y^1$, $Z^1$, Ar, $R^{20}$, k, m, n, p, q, r, s, t and $R^1$ to $R^{16}$ in Formulae (A), (B) and (C); and x, y and z are molar fractions relative to the total x+y+z=100 mol %.

In the polymer, the repeating structural units of Formula (A), namely, the units expressed with x account for 0.5 to 99.9 mol %, preferably 10 to 99.5 mol %, and the repeating structural units of Formula (C), namely, the units expressed with z account for 0.1 to 99.5 mol %, preferably 0.5 to 89.5 mol %. The repeating structural units of Formula (B), namely, the units expressed with y are optional and may comprise an arbitrary proportion corresponding to the remaining balance after the subtraction of the units (A) and (C). Where present, the repeating units desirably account for 99.4 to 0.01 mol %, preferably 89.5 to 0.5 mol %.

The repeating structural units of Formula (C), namely, the units expressed with z account for 0.001 to 50 mol %, preferably 0.1 to 30 mol %, more preferably 1 to 25 mol % relative to the repeating structural units of Formula (A), namely, the units expressed with x.

The polymer usually has an ion exchange capacity of 0.3 to 5 meq/g, preferably 0.5 to 3 meq/g, more preferably 0.8 to 2.8 meq/g. Ion exchange capacity less than 0.3 meq/g gives low proton conductivity and low generating performance. Ion exchange capacity exceeding 5 meq/g may result in drastically deteriorated water resistance.

The ion exchange capacity may be controlled by changing the kinds, amounts and combination of the structural units (A), (B) and (C). That is, the ion exchange capacity may be controlled by changing the feeding amounts and kinds of precursors (monomers, oligomers) from which the structural units (A) to (C) are derived in the polymerization.

In general, the more the structural units (A), the higher the ion exchange capacity and the proton conductivity, but the lower the water resistance. On the other hand, the less the structural units (A), the lower the ion exchange capacity and the higher the water resistance, but the lower the proton conductivity.

The presence of the structural units (C) improves the stability of the sulfonic acid groups at high temperatures, and thus gives improved heat resistance. The nitrogen atom in the nitrogen-containing heterocyclic aromatic compound has basicity, and has an ionic interaction with the sulfonic acid group. This interaction increases the stability of the sulfonic acid groups and inhibits the detachment of the sulfonic acid groups at high temperatures. Furthermore, the interaction prevents crosslinking reaction between polymer molecules at the sulfonic acid groups at high temperatures. The nitrogen-containing heterocyclic aromatic compound possesses appropriate basicity that is as strong as these advantages are obtained without deteriorating the proton conductivity.

The structural units (B) are optional and may not be used. The proportion of the structural units (B) corresponds to the remaining balance after the subtraction of the units (A) and (C) from the polymer. The structural units (B) give easy control of the molecular weight and the contents of the other repeating units. The polymer including the structural units (B) shows thermal and chemical stability.

The polymer has a polystyrene equivalent weight-average molecular weight of 10,000 to 1,000,000, preferably 20,000 to 800,000 as measured by gel permeation chromatography (GPC).

<Production of Polymer>

The polymer having sulfonic acid groups may be produced by the following methods A, B and C, which are exemplary.

(Method A)

A monomer of Formula (A'), a monomer of Formula (B') and a monomer of Formula (C') are copolymerized to give a polymer with sulfonate groups. The sulfonate groups are de-esterified into sulfonic acid groups. This method is described in JP-A-2004-137444.

Monomer (A')

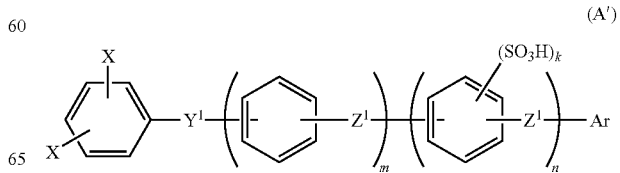

(A')

X is an atom or a group selected from a chlorine atom, a bromine atom and —OSO₂Rb (wherein Rb is an alkyl group, a fluorine-substituted alkyl group or an aryl group). $Y^1$, $Z^1$, Ar, m, n and k are as described in Formula (A). R is an alkyl group of 4 to 12 carbon atoms.

Specific examples of the compounds represented by Formula (A') include those represented by the formulae below, and sulfonates described in JP-A-2004-137444, JP-A-2004-345997 and JP-A-2004-346163.

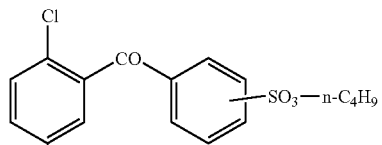

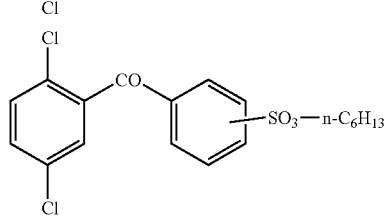

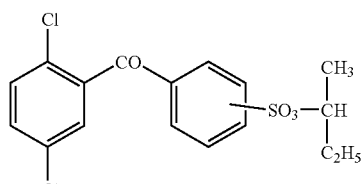

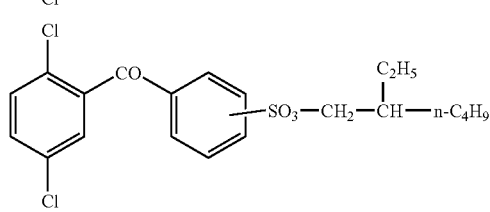

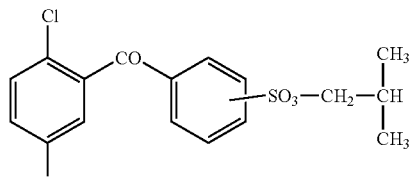

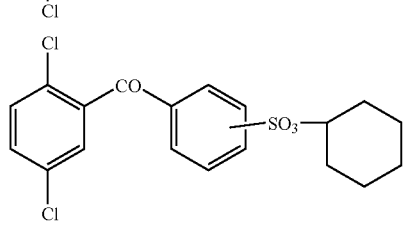

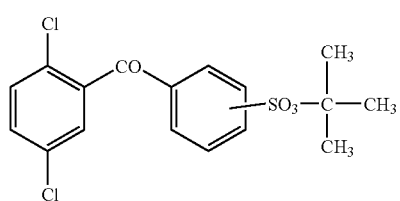

-continued

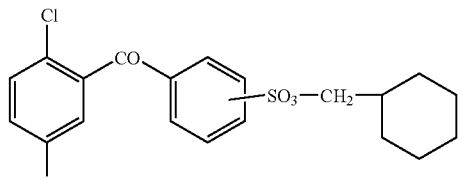

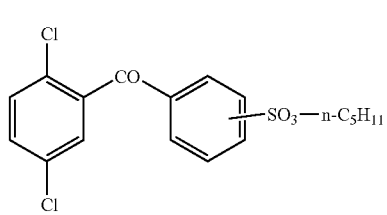

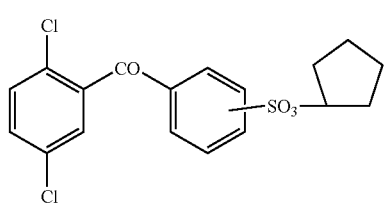

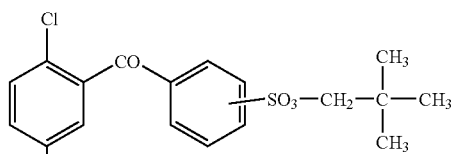

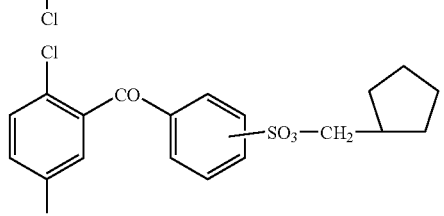

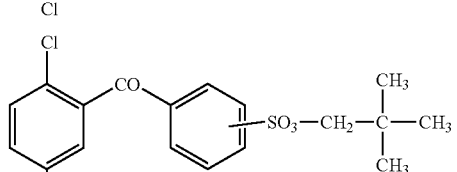

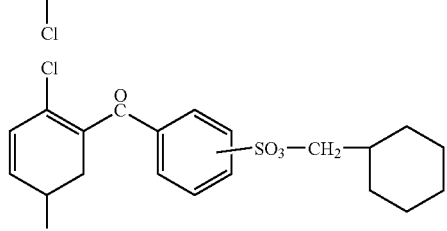

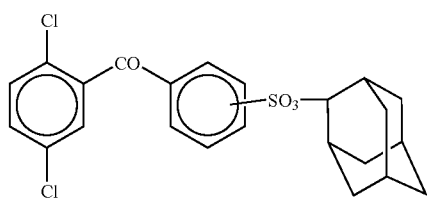

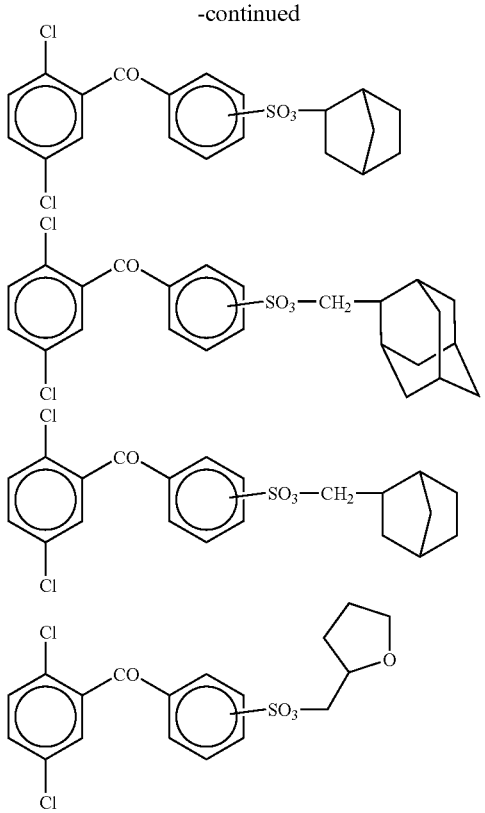

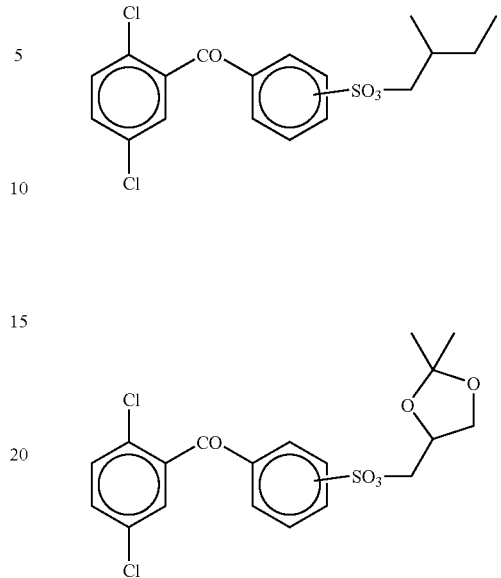

In the compounds represented by Formula (A'), the sulfonate structure is generally bonded to the meta position of the aromatic ring.

Monomer (B')

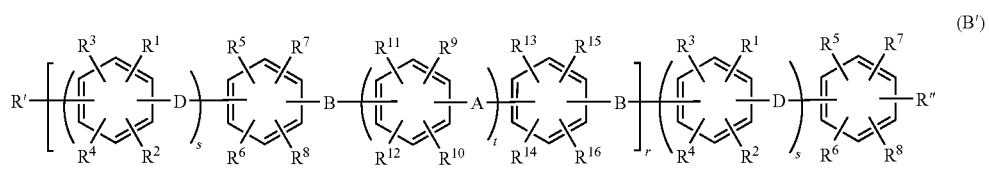

R' and R" are each an atom or a group selected from a chlorine atom, a bromine atom and —$OSO_2Rb$ (wherein Rb is an alkyl group, a fluorine-substituted alkyl group or an aryl group).

$R^1$ to $R^{16}$, A, B, D, s, t and r are as described in Formula (B).

Specific examples of the monomers (B') represented by Formula (B') wherein r is 0 include 4,4'-dichlorobenzophenone, 4,4'-dichlorobenzanilide, 2,2-bis(4-chlorophenyl)difluoromethane, 2,2-bis(4-chlorophenyl)-1,1,1,3,3,3-hexafluoropropane, 4-chlorobenzoic acid-4-chlorophenyl ester, bis(4-chlorophenyl)sulfoxide, bis(4-chlorophenyl)sulfone and 2,6-dichlorobenzonitrile. In these compounds, the chlorine atoms may be replaced by bromine atoms or iodine atoms.

Examples of the compounds of Formula (B') wherein r is 1 include those represented by the formulae below and those described in JP-A-2003-113136.

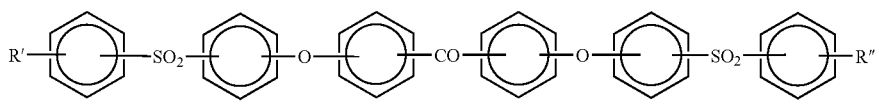

-continued
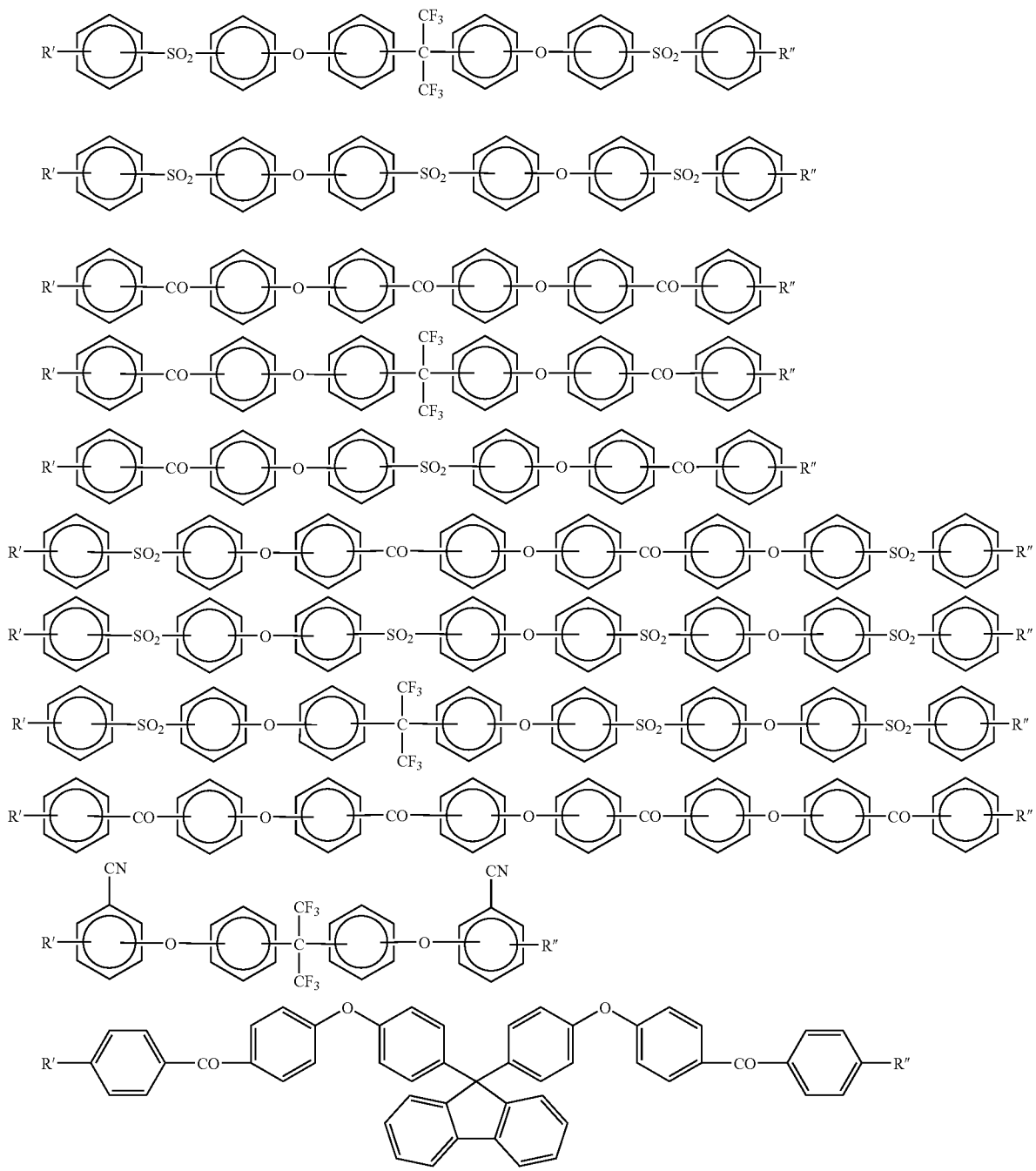
Examples of the compounds of Formula (B') wherein $r \geqq 2$ include those represented by the formulae below:
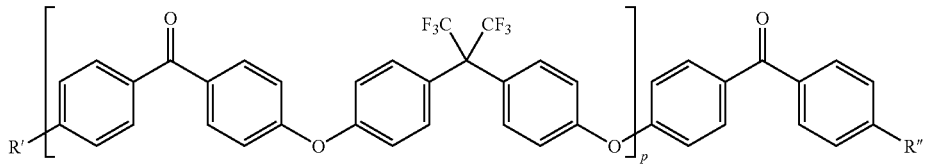

-continued

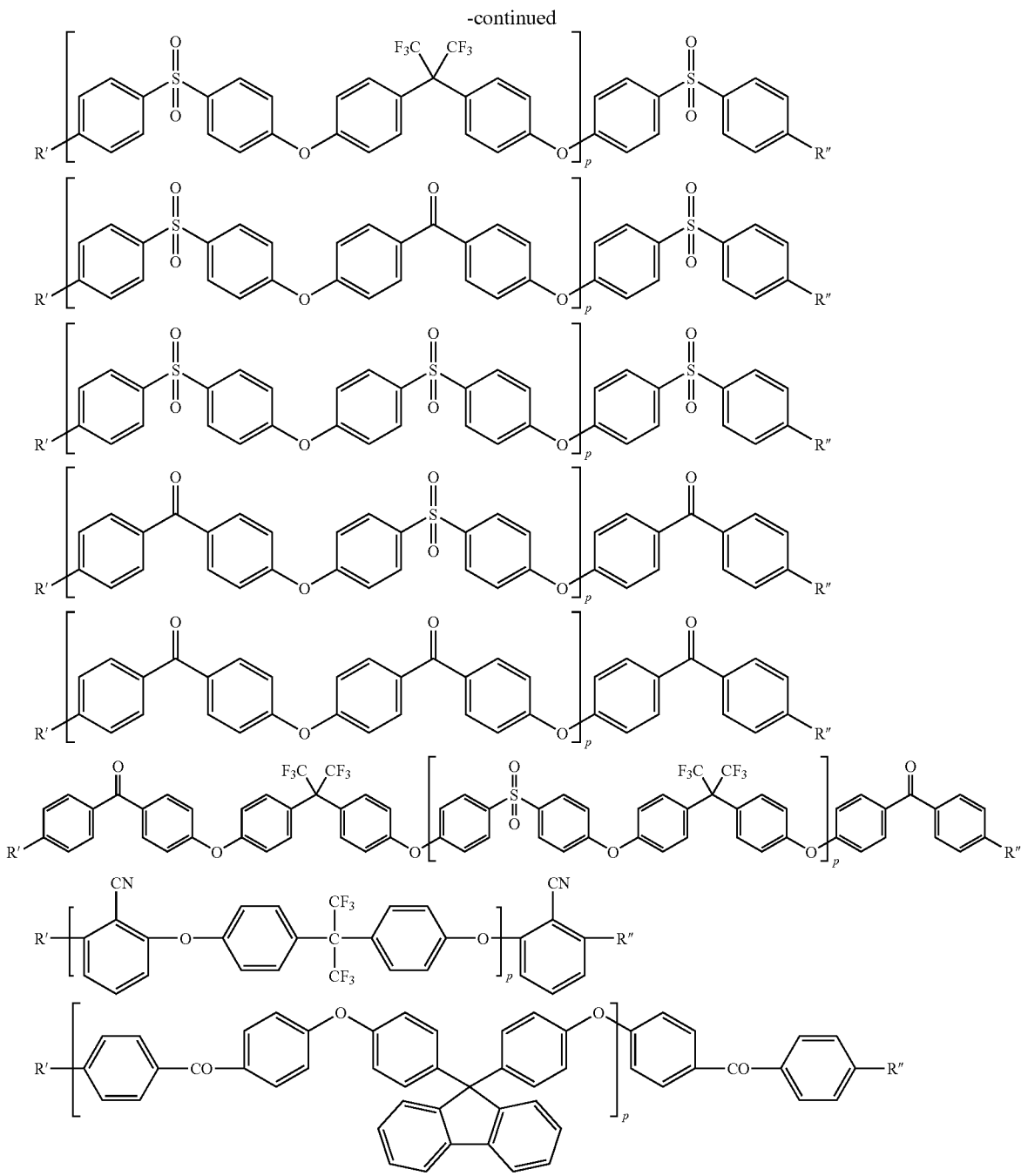

Monomer (C')

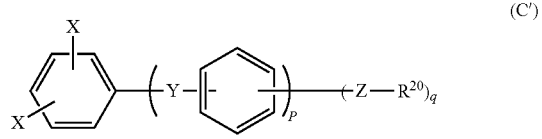

X is an atom or a group selected from a chlorine atom, a bromine atom and —OSO$_2$Rb (wherein Rb is an alkyl group, a fluorine-substituted alkyl group or an aryl group).

Y, Z, R$^{20}$, p and q are as described in Formula (C).

Examples of the monomers (C) include the nitrogen-containing aromatic compounds represented by Formula (1).

Polymerization

In the production of the polymer of the present invention, the monomer (A'), the monomer (C') and optionally the monomer (B') are copolymerized to give a precursor.

The copolymerization is performed in the presence of a catalyst. The catalyst used in the copolymerization is a catalyst system containing a transition metal compound. This catalyst system essentially contains (1) a transition metal salt and a compound as a ligand (hereinafter, the ligand component), or a transition metal complex (which may be a copper salt) in which a ligand is coordinated, and (2) a reducing agent. A "salt" may be added to increase the polymerization rate.

Specific examples of the catalyst components, amounts of the components, reaction solvents, concentrations, temperatures, reaction time and other polymerization conditions are described in JP-A-2001-342241.

Preferred examples of the transition metal salts include nickel chloride and nickel bromide. Preferred examples of the ligand compounds include triphenylphosphine, tri-o-tolylphosphine, tri-m-tolylphosphine, tri-p-tolylphosphine, tributylphosphine, tri-tert-butylphosphine, trioctylphosphine and 2,2'-bipyridine. Preferred examples of the transition metals (salts) with a coordinated ligand include nickel chloride bis(triphenylphosphine) and nickel chloride (2,2'-bipyridine). Examples of the reducing agents include iron, zinc, manganese, aluminum, magnesium, sodium and calcium, with zinc, magnesium and manganese being preferable. Preferred examples of the "salts" include sodium bromide, sodium iodide, potassium bromide, tetraethylammonium bromide and tetraethylammonium iodide. The reaction may involve a polymerization solvent, with examples including tetrahydrofuran, N,N-dimethylformamide, N,N-dimethylacetamide and 1-methyl-2-pyrrolidone.

The catalyst system contains the components in amounts described below. The amount of the transition metal salt or the transition metal (salt) with a coordinated ligand is generally 0.0001 to 10 mol, preferably 0.01 to 0.5 mol based on 1 mol of the monomers combined. This amount gives high catalytic activity and high molecular weight. When the catalyst system includes the "salt", the amount of the salt is generally 0.001 to 100 mol, preferably 0.01 to 1 mol based on 1 mol of the monomers combined. When the amount is in this range, the catalyst system provides a sufficiently high polymerization rate. The concentration of the monomers combined in the polymerization solvent is generally 1 to 90 wt %, preferably 5 to 40 wt %. The polymerization temperature in producing the polymer is generally 0 to 200° C., preferably 50 to 100° C. The polymerization time is generally from 0.5 to 100 hours, preferably 1 to 40 hours.

The polymer obtained is then hydrolyzed to convert the sulfonate groups (—$SO_3R$) of the structural units to the sulfonic acid groups (—$SO_3H$).

The hydrolysis may be performed by any of the following methods: (1) the polymer with sulfonate groups is added to an excess of water or an alcohol that contains a small amount of hydrochloric acid, and the mixture is stirred for at least 5 minutes; (2) the polymer with sulfonate groups is reacted in trifluoroacetic acid at about 80 to 120° C. for about 5 to 10 hours; and (3) the polymer with sulfonate groups is reacted in a solution such as N-methylpyrrolidone that contains lithium bromide in a molar amount 1 to 3 times that of the sulfonate groups (—$SO_3R$) of the polymer, at about 80 to 150° C. for about 3 to 10 hours, and thereafter hydrochloric acid is added to the reaction product.

(Method B)

A monomer having a skeleton represented by Formula (A') except that the monomer has no sulfonic acid groups or sulfonate groups, and the monomers (B') and (C') are copolymerized. The copolymer obtained is sulfonated with a sulfonating agent. This method is described in JP-A-2001-342241.

In Method B, specific examples of the monomers without sulfonic acid groups or sulfonate groups that are capable of forming the structural units of Formula (A) include dihalides described in JP-A-2001-342241 and JP-A-2002-293889.

(Method C)

This method is useful when Ar in Formula (A) is an aromatic group having a substituent —$O(CH_2)_nSO_3H$ or —$O(CF_2)_nSO_3H$. A monomer of a precursor capable of forming the structural units of Formula (A), a monomer or oligomer capable of forming the structural units of Formula (B), and a monomer capable of forming the structural units of Formula (C) are copolymerized. Subsequently, an alkylsulfonic acid or a fluorine-substituted alkylsulfonic acid is introduced into the copolymer. This method is described in JP-A-2005-606254.

In Method C, examples of the monomers of precursors capable of forming the structural units of Formula (A) include dihalides described in JP-A-2005-36125. Specific examples include 2,5-dichloro-4'-hydroxybenzophenone, 2,4-dichloro-4'-hydroxybenzophenone, 2,6-dichloro-4'-hydroxybenzophenone, 2,5-dichloro-2',4'-dihydroxybenzophenone, and 2,4-dichloro-2',4'-dihydroxybenzophenone. Examples further include compounds corresponding to the above compounds except that the hydroxyl group(s) is protected with a tetrahydropyranyl group or the like, compounds corresponding to the above compounds except that the hydroxyl group(s) is replaced by a thiol group, and compounds corresponding to the above compounds except that the chlorine atom(s) is replaced by a bromine atom or an iodine atom.

In Method C, alkylsulfonic acid groups are introduced into the precursor polymer (without sulfonic acid groups) by a method described in JP-A-2005-60625. For example, the objective groups may be introduced by reacting the hydroxyl groups of the precursor polymer with propane sultone, butane sultone or the like.

<Proton Conductive Membrane>

The proton conductive membrane according to the present invention comprises the polymer having the sulfonic acid groups and the nitrogen-containing heterocyclic groups.

The proton conductive membrane of the invention may be produced by any methods without limitation. As an example, a casting method is generally used in which the polymer of the invention is dissolved in an organic solvent, the solution is cast over a substrate, and the film is dried by removing the solvent.

The substrate used in the membrane production is not particularly limited as long as it is commonly used in the usual solution casting methods. For example, plastic substrates and metal substrates may be used, and thermoplastic resin substrates such as polyethyleneterephthalate (PET) films may be preferably used.

Examples of the solvents used in the membrane production include aprotic polar solvents such as N-methyl-2-pyrrolidone, N,N-dimethylformamide, γ-butyrolactone, N,N-dimethylacetamide, dimethylsulfoxide, dimethylurea and dimethylimidazolidinone. In view of solvent properties and solution viscosity, N-methyl-2-pyrrolidone (hereinafter "NMP") is particularly preferable. The aprotic polar solvents may be used singly or two or more kinds may be used in combination.

The solvent may be a mixed solvent of the above aprotic polar solvent and an alcohol. Examples of the alcohols include methanol, ethanol, propyl alcohol, isopropyl alcohol, sec-butyl alcohol and tert-butyl alcohol. In particular, methanol is preferable since it gives an appropriately low solution viscosity over a wide range of proportions of the polymer. These alcohols may be used singly or two or more kinds may be used in combination.

The above mixed solvent will contain the aprotic polar solvent in an amount of 95 to 25 wt %, preferably 90 to 25 wt %, and the alcohol in an amount of 5 to 75 wt %, preferably 10 to 75 wt % (the total is 100 wt %). This proportion of the alcohol leads to an appropriately low solution viscosity.

In addition to the alcohols, inorganic acids such as sulfuric acid and phosphoric acid, organic acids including carboxylic acids, and appropriate amounts of water may be used in combination.

The concentration of the polymer in the solution (i.e. the polymer concentration) is generally from 5 to 40 wt %, preferably from 7 to 25 wt %. The polymer concentration less than 5 wt % causes difficulties in producing the membrane in large thickness and will result in pinholes. On the other hand, when the polymer concentration exceeds 40 wt %, the solution viscosity becomes so high that the film production will be difficult and the obtained film may have low surface smoothness.

The solution viscosity generally ranges from 2,000 to 100,000 mPa·s, preferably from 3,000 to 50,000 mPa·s. When the solution viscosity is less than 2,000 mPa·s, the solution will have so high fluidity that it may spill out of the substrate during the membrane production. On the other hand, the solution viscosity exceeding 100,000 mPa·s is so high that the solution cannot be extruded through a die and the flow-casting for the film production may be difficult.

The wet film obtained as described above may be immersed in water to substitute the organic solvent in the film with water. This treatment reduces the amount of the residual solvent in the proton conductive membrane. Before the wet film is immersed in water, it may be predried. The predrying may be performed by subjecting the wet film at 50 to 150° C. for 0.1 to 10 hours.

Immersing the wet films (or the predried films, the same applies hereinafter) in water may be carried out batchwise with respect to each sheet, or may be a continuous process wherein the films, which may be in the original form of laminate with the substrate film (e.g. PET film) as produced or which may be released from the substrate, are immersed in water and are wound sequentially. In the batchwise immersing, the wet films are preferably framed or fixed by similar means to prevent wrinkles from forming on the surface of the treated films.

The immersing will be suitably made so that the wet films will contact water that is at least 10 parts by weight, preferably at least 30 parts by weight, more preferably at least 50 parts by weight based on 1 part by weight of the wet films. This amount of water sufficiently reduces the residual solvent in the proton conductive membrane. In order to reduce the residual solvent in the proton conductive membrane, it is also effective to keep the concentration of the organic solvent in water at or below a certain level by renewing water used in the immersing or by overflowing water. The in-plane distribution of the residual organic solvent in the proton conductive membrane may be effectively uniformed by homogenizing the organic solvent concentration in the water by stirring or the like.

When the wet film is immersed in water, the water temperature is usually 5 to 80° C., preferably 10 to 60° C. in view of substitution rate and easy handling. Although a higher temperature accelerates the substitution between the organic solvent and water, the water absorption of the film will also increase at higher temperatures. There is thus a concern that the proton conductive membrane has a rough surface after dried. The immersing time varies depending on the initial amount of residual solvent, the water amount and the treatment temperature. In general, the immersing time ranges from 10 minutes to 240 hours, preferably from 30 minutes to 100 hours.

After the wet film is immersed in water as described above, the film is dried at 30 to 100° C., preferably 50 to 80° C., for 10 to 180 minutes, preferably 15 to 60 minutes. Subsequently, the film is vacuum dried at 50 to 150° C. and preferably at 500 to 0.1 mmHg for 0.5 to 24 hours. The proton conductive membrane according to the invention may be thus obtained.

The proton conductive membrane obtained as described above generally contains the residual solvent at not more than 5 wt %, preferably not more than 1 wt %.

The proton conductive membrane generally ranges in dry thickness from 10 to 100 μm, preferably from 20 to 80 μm.

EXAMPLES

The present invention will be described in detail by examples below, but it should be construed that the invention is in no way limited to such examples.

Example 1-1

Synthesis of 2,5-dichloro-4'-(1-imidazolyl)benzophenone

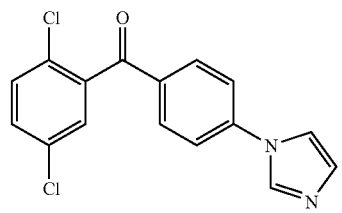

A 2-L three-necked flask equipped with a stirrer, a thermometer, a condenser tube and a nitrogen inlet tube was charged with 150.7 g (0.560 mol) of 2,5-dichloro-4'-fluorobenzophenone, 114.4 g (1.68 mol) of imidazole, 100.6 g (0.728 mol) of potassium carbonate and 840 ml of N,N'-dimethylacetamide. The reaction solution was heated under a nitrogen atmosphere in an oil bath at 110° C. for 2 hours. After thin layer chromatography confirmed that the materials showed no peaks, the reaction liquid was allowed to cool to room temperature. The reaction liquid was slowly added to 3 L of water, and the product was precipitated. The liquid was then filtered. The product obtained by the filtration was dissolved in THF (1.2 L), and toluene (4 L) was added to the solution. The mixture was washed with salt solution until the water phase became neutral. The organic phase was dried over magnesium sulfate, and the solvent was evaporated with an evaporator. A crude product weighing 180 g was obtained. The crude product was subjected to recrystallization using 1 L of toluene and 20 ml of methanol in combination at 80° C., and the resultant crystal was isolated. As a result, 155 g of a white solid was obtained with a yield of 87%. A $^1$H-NMR spectrum of the compound is shown in FIG. 1.

Example 1-2

Synthesis of 2,5-dichloro-4'-(1-pyrrolyl)benzophenone

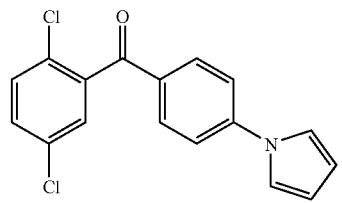

A 2-L three-necked flask equipped with a stirrer, a thermometer, a condenser tube and a nitrogen inlet tube was charged with 134.6 g (0.500 mol) of 2,5-dichloro-4'-fluorobenzophenone, 50.3 g (0.750 mol) of pyrrole, 76.0 g (0.550 mol) of potassium carbonate and 840 ml of dehydrated N,N'-dimethylacetamide. The reaction solution was heated under a nitrogen atmosphere in an oil bath at 100° C. for 3 hours. After thin layer chromatography confirmed that the materials showed no peaks, the reaction liquid was allowed to cool to room temperature. The reaction liquid was slowly added to 3 L of water, and the product was precipitated. The liquid was then filtered. The product obtained by the filtration was dissolved in 2.5 L of toluene. The solution was washed with salt solution using a separating funnel until the water phase became neutral. The organic phase was dried over magnesium sulfate, and the solvent was evaporated with an evaporator. A crude product weighing 133.3 g was obtained. The crude product was subjected to recrystallization using a hexane/ethyl acetate mixed solvent, and the resultant crystal was isolated. As a result, 125.3 g (0.396 mol) of an objective purified product was obtained with a yield of 79.3%.

Example 1-3

Synthesis of 2,5-dichloro-4'-(2-benzothiazolylthioxy)benzophenone

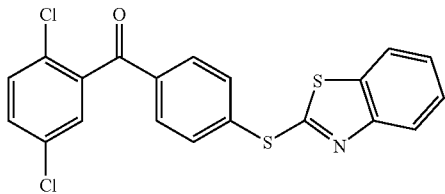

A 3-L three-necked flask equipped with a stirrer, a thermometer, a condenser tube and a nitrogen inlet tube was charged with 269.1 g (1.000 mol) of 2,5-dichloro-4'-fluorobenzophenone, 175.6 g (1.050 mol) of 2-mercaptobenzothiazole, 152.0 g (1.100 mol) of potassium carbonate and 1500 ml of dehydrated N,N'-dimethylacetamide. The reaction solution was heated under a nitrogen atmosphere in an oil bath at 110° C. for 2 hours. After thin layer chromatography confirmed that the materials showed no peaks, the reaction liquid was allowed to cool to room temperature. The reaction liquid was slowly added to 3 L of water, and the product was precipitated. The liquid was then filtered. The product obtained by the filtration was dissolved in 4 L of toluene. The organic phase (toluene solution of the product) was washed with salt solution until neutrality was reached. The organic phase was dried over magnesium sulfate, and the solvent was evaporated with an evaporator. A crude product weighing 350.3 g was obtained. The crude product was subjected to recrystallization using 1.5 L of toluene heated at 80° C., and the resultant crystal was isolated. As a result, 325.4 g (0.782 mol) of a purified product was obtained with a yield of 78.2%.

Polymers will be described in Examples below. Evaluation membranes were prepared as described below. The sulfonic acid equivalent, molecular weight and proton conductivity were measured as described below.

<Preparation of Membranes>

Sulfonated polymers gave membranes in the following manner. A 15 wt % solution of the sulfonated polymer (the solvent was a mixture of methanol/NMP=50/50 (volume ratio)) was cast to form a membrane. The membrane was immersed in a large quantity of distilled water overnight. This dilution removed residual NMP in the membrane. The membrane was dried (thickness: 40 μm)

In Examples, proton conductive membranes were prepared from a nitrogen-containing heterocyclic aromatic compound and a sulfonated polymer in the following manner. A predetermined amount of the nitrogen-containing heterocyclic aromatic compound, and the sulfonated polyarylene were dissolved in a mixture of methanol/NMP=50/50 (volume ratio) to a polymer concentration of 15 wt %. The thus-prepared varnish was cast to give a membrane. The membrane was immersed in a large quantity of distilled water. This dilution removed residual NMP in the membrane. An objective membrane was thus obtained (thickness: 40 μm).

<Sulfonic Acid Equivalent>

The polymer having sulfonic acid groups was washed until the washings became neutral, and the free residual acids were removed. The polymer was sufficiently washed with water and was dried. A predetermined amount of the polymer was weighed out and was dissolved in a THF/water mixed solvent. The solution was titrated with an NaOH standard solution using phenolphthalein as an indicator. The sulfonic acid equivalent was determined from the point of neutralization.

<Measurement of Molecular Weight>

For the polymers having no sulfonic acid groups, the polystyrene equivalent weight-average molecular weight was determined by GPC using tetrahydrofuran (THF) as solvent.

For the polymers having sulfonic acid groups and for the thermally tested polymers having sulfonic acid groups, the polystyrene equivalent molecular weight was determined by GPC using an eluting solution which was a mixed solvent consisting of 7.83 g of lithium bromide, 3.3 ml of phosphoric acid and 2 L of N-methyl-2-pyrrolidone (NMP).

<Measurement of Resistivity>

A 5 mm-wide strip specimen of the proton conductive membrane, holding 5 platinum wires (0.5 mm diameter) at intervals of 5 mm on its surface, was placed in a thermohygrostat. Subsequently, the alternating current impedance between the platinum wires was measured at 85° C., 90% RH and 10 kHz. This measurement was carried out using a chemical impedance measuring system (NF Corporation) and thermo-hygrostat JW241 (Yamato Science Co., Ltd.). The alternating current resistance was measured in each case where the interwire distance was varied from 5 mm to 20 mm among the 5 platinum wires. The resistivity of the membrane was calculated from a gradient between the interwire distance and the resistance.

Resistivity $R(\Omega\cdot cm)=0.5$ (cm)×membrane thickness (cm)×resistance/interwire distance gradient $(\Omega/cm)$ <Evaluation of Heat Resistance>

The films approximately 40 μm in thickness were each placed in an oven at 160° C. for 24 hours. Before and after the heat resistance test, the samples were immersed and dissolved in the aforementioned NMP-based GPC eluting solution in a ratio of 99.8 parts by weight of the eluting solution and 0.2 part by weight of the proton conductive membrane. Insolubles were removed, and the solutions were subjected to GPC. The content of insolubles was determined from a ratio of the areas assigned to the components eluted in GPC before and after the heat resistance test.

Example 2-1

(1) Synthesis of Nitrogen-containing Heterocyclic Group-containing Sulfonated Polymer A-N1

A three-necked flask equipped with a condenser tube and a three-way cock was charged with 185.3 g (0.540 mol) of 2,5-dichloro-4'-phenoxybenzophenone, 15.1 g (0.060 mol) of 4,4'-dichlorobenzophenone, 7.1 g (0.024 mol) of 2,5-dichloro-4'-(1-pyrrolyl)benzophenone obtained in Example 1-2, 11.7 g (0.078 mol) of sodium iodide, 11.8 g (0.018 mmol) of bis(triphenylphosphine)nickel dichloride, 63.0 g (0.240 mol) of triphenylphosphine and 94.1 g (1.440 mol) of zinc. The flask was placed in an oil bath at 70° C. and was purged with nitrogen. Under the nitrogen atmosphere, 1000 ml of N-methyl-2-pyrrolidone was added, and the reaction was initiated. After 20 hours, the system was diluted with 500 ml of N-methyl-2-pyrrolidone. The polymerization liquid was poured into a 1:10 hydrochloric acid/methanol solution, and the polymer was precipitated. The polymer was washed, filtered and vacuum dried to give white powder. The powder weighed 148 g. The weight-average molecular weight was 154,000. To 150 g of the polymer, 1500 ml of concentrated sulfuric acid was added. The mixture was stirred at room temperature for 24 hours for sulfonation. After the reaction, the reaction liquid was poured into a large quantity of purified water, and the sulfonated polymer was precipitated. The polymer was washed with purified water until pH 7 was reached. The sulfonated polymer was filtered, collected and vacuum dried at 90° C. The sulfonated polymer weighed 159 g. The polymer had an ion exchange capacity of 2.3 meq/g, and a weight-average molecular weight of 185,000. The polymer is represented by Structural formula (A-N1). This polymer having sulfonic acid groups will be referred to as the polymer A-N1.

Structural Formula A-N1

Polymer A-N1

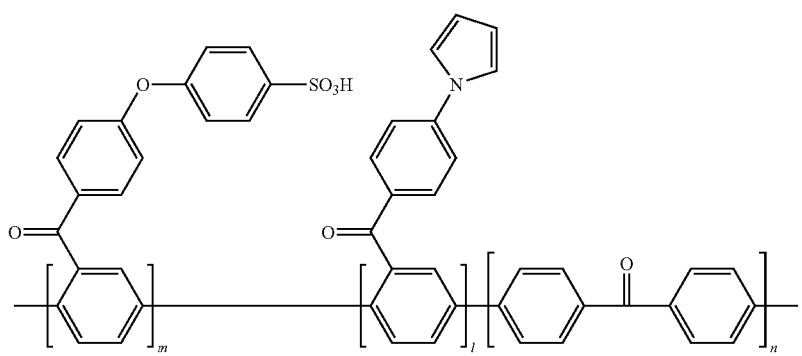

(2) Evaluation of Properties of Nitrogen-containing Heterocyclic Group-containing Sulfonated Polymer A-N1

The nitrogen-containing heterocyclic group-containing sulfonated polymer A-N1 was dissolved in a mixture of methanol/NMP=50/50 to a concentration of 15 wt %. The thus-prepared varnish was cast to give a membrane. The membrane was immersed in a large quantity of distilled water. This dilution removed residual NMP in the membrane. An objective membrane having a thickness of 40 μm was thus obtained. The membrane was evaluated for resistivity and heat resistance. The results are shown in Table 1.

Example 2-2

(1) Synthesis of Hydrophobic Units B

A 1-L three-necked flask equipped with a stirrer, a thermometer, a Dean-stark tube, a nitrogen inlet tube and a condenser tube was charged with 29.8 g (0.104 mol) of 4,4'-dichlorodiphenylsulfone, 37.4 g (0.111 mol) of 2,2-bis(4-hydroxyphenyl)-1,1,1,3,3,3-hexafluoropropane and 20.0 g (0.145 mol) of potassium carbonate. The flask was purged with nitrogen, and 168 mL and 84 mL of sulfolane and toluene, respectively, were added, followed by stirring. The flask was placed in an oil bath, and the reaction liquid was heated under reflux at 150° C. Byproduct water was trapped in the Dean-stark tube. Water generation was stopped after 3 hours. Thereafter, toluene was removed from the system through the Dean-stark tube. The reaction temperature was gradually raised to 200° C. and the stirring was continued for 5 hours. Subsequently, 7.5 g (0.030 mol) of 4,4'-dichlorobenzophenone was added, and the reaction was performed for another 8 hours. The reaction liquid was allowed to cool and was diluted with 100 mL of toluene. The reaction liquid was filtered to remove insoluble inorganic salts. The filtrate was poured into 2 L of methanol, and the product was precipitated. The precipitated product was filtered and was dried. The product was dissolved in 250 mL of tetrahydrofuran and was reprecipitated as white powder in 2 L of methanol. The powder was filtered and was dried. As a result, 56 g of hydrophobic units B were obtained. The number-average molecular weight (Mn) by GPC was 10,500. The compound is represented by Formula (B-1).

Structural Formula B-1

Hydrophobic units B

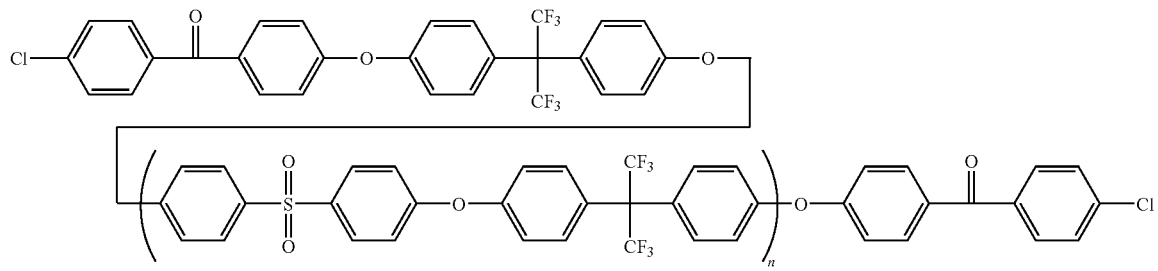

(2) Synthesis of Nitrogen-containing Heterocyclic Group-containing Sulfonated Polymer B-N1

A 1-L three-necked flask equipped with a stirrer, a thermometer and a nitrogen inlet tube was charged with 141.6 g (0.338 mol) of neopentyl 3-(2,5-dichlorobenzoyl)benzenesulfonate, 44.5 g (4.2 mmol) of the hydrophobic units B (Mn: 10,500) obtained above, 5.4 g (16.9 mmol) of 2,5-dichloro-4'-(1-imidazolyl)benzophenone obtained in Example 1-1, 6.71 g (10.3 mmol) of bis(triphenylphosphine)nickel dichloride, 1.54 g (10.3 mmol) of sodium iodide, 35.9 g (137 mmol) of triphenylphosphine and 53.7 g (820 mmol) of zinc. The flask was purged with dry nitrogen. To the flask, 430 mL of N,N-dimethylacetamide (DMAc) was added. The system was stirred for 3 hours while the reaction temperature was maintained at 80° C. The reaction liquid was diluted with 730 mL of DMAc, and insolubles were filtered.

The solution obtained was introduced into a 2-L three-necked flask equipped with a stirrer, a thermometer and a nitrogen inlet tube. The solution was heated to 115° C. with stirring, and 44 g (506 mmol) of lithium bromide was added. The mixture was stirred for 7 hours and was poured into 5 L of acetone, and the product was precipitated. The product was sequentially washed with 1N hydrochloric acid and with purified water, and was dried. As a result, an objective sulfonated polymer weighing 124 g was obtained. The weight-average molecular weight (Mw) of the polymer was 166,000. The sulfonated polymer was assumed to be represented by Formula (II). The polymer had an ion exchange capacity of 2.3 meq/g. The polymer having sulfonic acid groups is represented by Structural formula B-N1. This polymer will be referred to as the polymer B-N1.

Structural Formula B-N1

This dilution removed residual NMP in the membrane. An objective membrane having a thickness of 40 μm was thus obtained. The membrane was evaluated for resistivity and heat resistance. The results are shown in Table 1.

Example 2-3

(1) Synthesis of Hydrophobic Units C

A 1-L three-necked flask equipped with a stirrer, a thermometer, a condenser tube, a Dean-stark tube and a nitrogen inlet three-way cock was charged with 67.3 g (0.200 mol) of 2,2-bis(4-hydroxyphenyl)-1,1,1,3,3,3-hexafluoropropane, 60.3 g (0.240 mol) of 4,4'-dichlorobenzophenone (4,4'-DCBP), 71.9 g (0.520 mol) of potassium carbonate, 300 mL of N,N-dimethylacetamide (DMAc) and 150 mL of toluene. The flask was placed in an oil bath, and reaction was performed by heating the reaction liquid under a nitrogen atmosphere at 130° C. with stirring. During the reaction, byproduct water was formed into an azeotropic mixture with toluene and the azeotropic mixture was removed from the system through the Dean-stark tube. Water generation was stopped after about 3 hours. While the reaction temperature was gradually raised 130° C. to 150° C., most of the toluene was removed. The reaction was carried out at 150° C. for 10 hours. Subsequently, 10.0 g (0.040 mol) of 4,4'-DCBP was added, and the reaction was carried out for another 5 hours. The reaction liquid was allowed to cool and was filtered to remove precipitated inorganic compounds which were byproducts. The filtrate was poured into 4 L of methanol. The precipitated product was filtered, collected and dried. The product was then Polymer B-N1

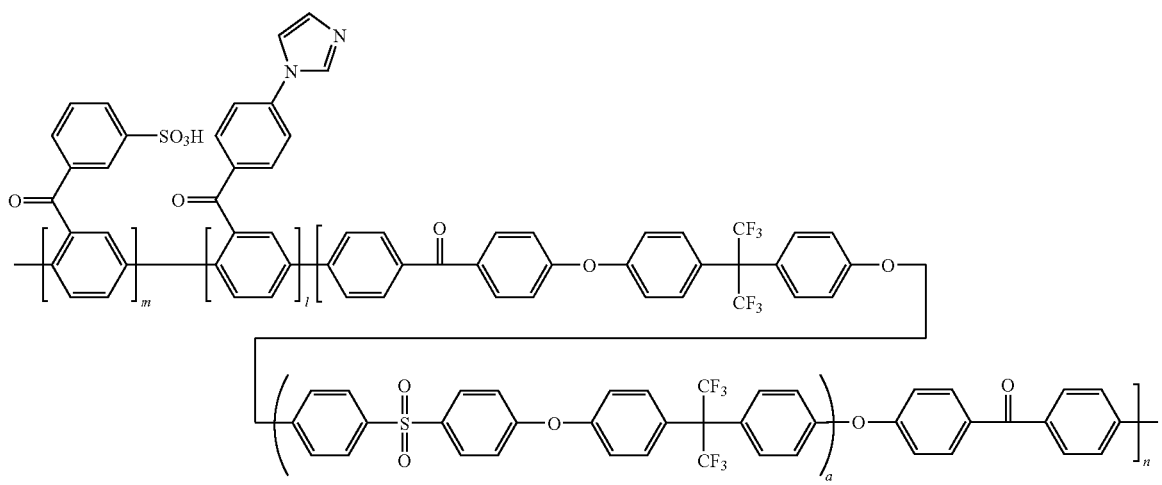

(3) Evaluation of properties of nitrogen-containing heterocyclic group-containing sulfonated polymer B-N1

The nitrogen-containing heterocyclic group-containing sulfonated polymer B-N1 was dissolved in a mixture of methanol/NMP=50/50 to a concentration of 15 wt %. The thus-prepared varnish was cast to give a membrane. The membrane was immersed in a large quantity of distilled water.

dissolved in 300 mL of tetrahydrofuran and was reprecipitated in 4 L of methanol. As a result, an objective compound weighing 95 g was obtained (yield: 85%).

The polymer had a polystyrene equivalent number-average molecular weight of 11,200 as measured by GPC (THF solvent). The compound was an oligomer represented by Structural formula C-1:

Structural Formula C-1

Hydrophobic units C

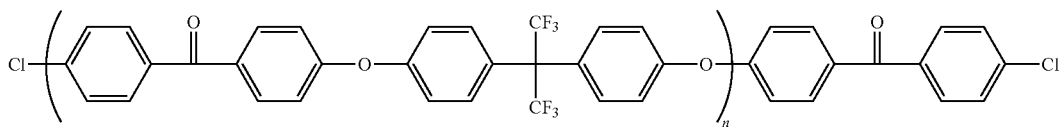

(2) Synthesis of Nitrogen-containing Heterocyclic Group-containing Sulfonated Polymer C-N1

Under a nitrogen atmosphere, 100 mL of dried N,N-dimethylacetamide (DMAc) was added to a mixture consisting of 27.21 g (0.039 mol) of a compound monomer C represented by Structural formula C-2 below, 16.13 g (1.44 mmol) of the hydrophobic units synthesized in (1), 0.80 g (1.93 mmol) of 2,5-dichloro-4'-(2-benzothiazolethioxy)benzophenone obtained in Example 1-3, 0.79 g (1.2 mmol) of bis(triphenylphosphine)nickel dichloride, 4.20 g (0.016 mol) of triphenylphosphine, 0.18 g (1.20 mmol) of sodium iodide and 6.28 g (96.1 mmol) of zinc.

The reaction system was heated (finally to 79° C.) with stirring, and reaction was performed for 3 hours. During the reaction, the viscosity of the system increased. The polymerization solution was diluted with 425 mL of DMAc, was stirred for 30 minutes and was filtered with use of Celite as a filter aid.

Part of the filtrate was poured into methanol, and the product was precipitated. The product was a copolymer comprising a sulfonic acid derivative protected with a neopentyl group. The copolymer had Mn of 57,500 and Mw of 175,300 as measured by GPC.

The filtrate was concentrated to 344 g with an evaporator and was combined with 10.1 g (0.116 mol) of lithium bromide. Reaction was performed at an internal temperature of 110° C. for 7 hours under a nitrogen atmosphere. After the reaction, the reaction liquid was cooled to room temperature and was poured into 4 L of acetone, and the product was precipitated. The product was filtered and was air dried. The product was then crushed with a mixer and was washed with 1500 mL of 1N hydrochloric acid with stirring. The product was filtered and was washed with ion exchange water until the washings had a pH of not less than 5. The product was dried at 80° C. overnight to give 23.0 g of an objective sulfonated polymer. This deprotected sulfonated polymer had Mn of 63,000 and Mw of 194,000. The polymer had an ion exchange capacity of 2.0 meq/g. The thus-obtained polymer C having sulfonic acid groups (Polymer CN-1) is represented as follows.

Structural Formula C-2

Monomer C

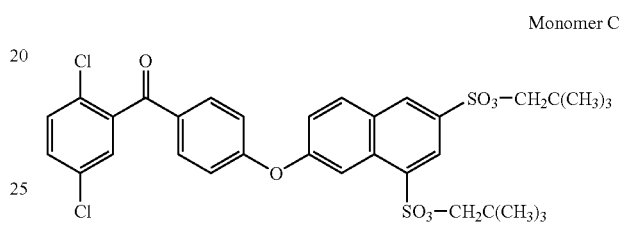

Structural formula C-N1

Polymer C-N1

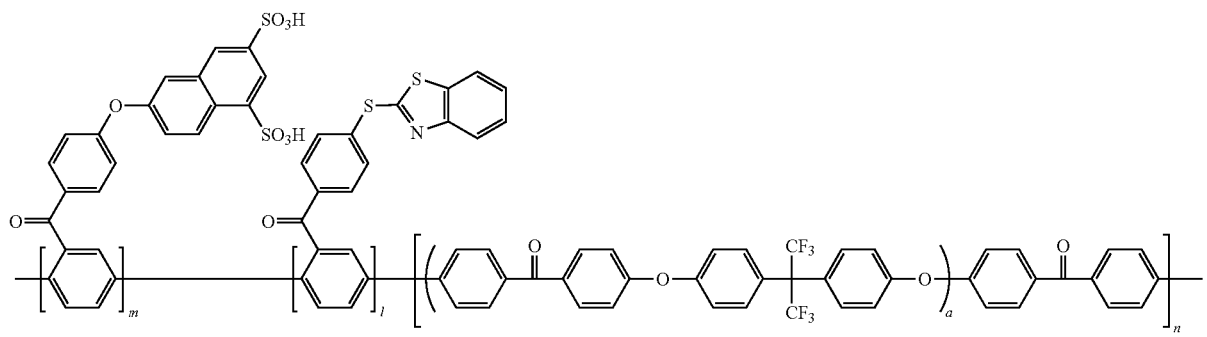

(3) Evaluation of Properties of Nitrogen-containing Heterocyclic Group-containing Sulfonated Polymer C-N1

The nitrogen-containing heterocyclic group-containing sulfonated polymer C-N1 was dissolved in a mixture of methanol/NMP=50/50 to a concentration of 15 wt %. The thus-prepared varnish was cast to give a membrane. The membrane was immersed in a large quantity of distilled water. This dilution removed residual NMP in the membrane. An objective membrane having a thickness of 40 μm was thus obtained. The membrane was evaluated for resistivity and heat resistance. The results are shown in Table 1.

Example 2-4

(1) Synthesis of Hydrophobic Units D

A 1-L three-necked flask equipped with a stirrer, a thermometer, a condenser tube, a Dean-stark tube and a nitrogen inlet three-way cock was charged with 49.4 g (0.29 mol) of 2,6-dichlorobenzonitrile, 88.4 g (0.26 mol) of 2,2-bis(4-hydroxyphenyl)-1,1,1,3,3,3-hexafluoropropane and 47.3 g (0.34 mol) of potassium carbonate. The flask was purged with nitrogen, and 346 mL and 173 mL of sulfolane and toluene, respectively, were added. The mixture was stirred. The flask was placed in an oil bath, and the reaction liquid was heated under reflux at 150° C. During the reaction, byproduct water was formed into an azeotropic mixture with toluene and the azeotropic mixture was removed from the system through the Dean-stark tube. Water generation was stopped after about 3 hours. While the reaction temperature was gradually raised, most of the toluene was removed. The reaction was carried out at 200° C. for 3 hours. Subsequently, 12.3 g (0.072 mol) of 2,6-dichlorobenzonitrile was added, and the reaction was carried out for another 5 hours.

The reaction liquid was allowed to cool and was diluted with 100 mL of toluene. The liquid was filtered to remove precipitated inorganic compounds which were byproducts. The filtrate was poured into 2 L of methanol. The precipitated product was filtered, collected and dried. The product was then dissolved in 250 mL of tetrahydrofuran and was reprecipitated in 2 L of methanol. As a result, an objective compound weighing 107 g was obtained.

The compound had a polystyrene equivalent number-average molecular weight of 7,300 as measured by GPC (THF solvent). The compound was an oligomer represented by The reaction system was heated (finally to 79° C.) with stirring, and reaction was performed for 3 hours. During the reaction, the viscosity of the system increased. The polymerization solution was diluted with 730 mL of DMAc, was stirred for 30 minutes and was filtered with use of Celite as a filter aid.

Part of the filtrate was poured into methanol, and the product was precipitated. The product was a copolymer comprising a sulfonic acid derivative protected with a neopentyl group. The copolymer had Mn of 58,000 and Mw of 135,300.

The filtrate was concentrated with an evaporator and was combined with 43.8 g (0.505 mol) of lithium bromide. Reaction was performed at an internal temperature of 110° C. for 7 hours under a nitrogen atmosphere. After the reaction, the reaction liquid was cooled to room temperature and was poured into 4 L of acetone, and the product was precipitated. The product was filtered and was air dried. The product was then crushed with a mixer and was washed with 1500 mL of 1N hydrochloric acid with stirring. The product was filtered and was washed with ion exchange water until the washings had a pH of not less than 5. The product was dried at 80° C. overnight to give 23.0 g of an objective sulfonated polymer. This deprotected sulfonated polymer had Mn of 60,000 and Mw of 175,000. The polymer had an ion exchange capacity of 2.4 meq/g. The thus-obtained polymer D-N1 having sulfonic acid groups is represented by Structural formula D-2.
Structural formula D-2

Polymer D-N1

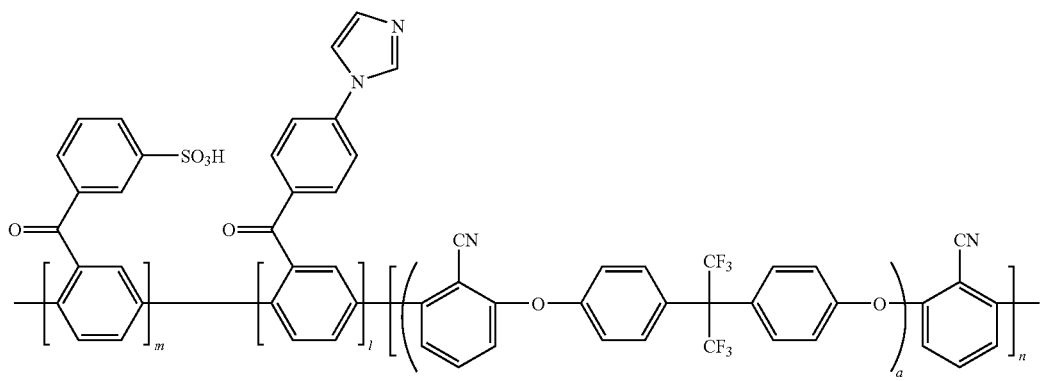

Structural formula D-1:
Structural formula D-1

Hydrophobic units D

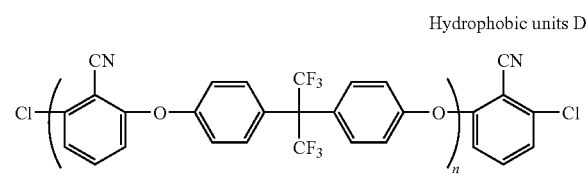

(2) Synthesis of Nitrogen-containing Heterocyclic Group-containing Sulfonated Polymer D-N1

Under a nitrogen atmosphere, 540 mL of dried N,N-dimethylacetamide (DMAc) was added to a mixture consisting of 135.0 g (0.336 mol) of neopentyl 3-(2,5-dichlorobenzoyl) benzenesulfonate, 40.7 g (5.6 mmol) of the hydrophobic units synthesized in (1), 6.71 g (16.8 mmol) of 2,5-dichloro-4'-(1-imidazolyl)benzophenone obtained in Example 1-2, 6.71 g (10.3 mmol) of bis(triphenylphosphine)nickel dichloride, 35.9 g (0.137 mol) of triphenylphosphine, 1.54 g (10.3 mmol) of sodium iodide and 53.7 g (0.821 mol) of zinc.

(3) Evaluation of Properties of Nitrogen-containing Heterocyclic Group-containing Sulfonated Polymer D-N1

The nitrogen-containing heterocyclic group-containing sulfonated polymer D-N1 was dissolved in a mixture of methanol/NMP=50/50 to a concentration of 15 wt %. The thus-prepared varnish was cast to give a membrane. The membrane was immersed in a large quantity of distilled water. This dilution removed residual NMP in the membrane. An objective membrane having a thickness of 40 μm was thus obtained. The membrane was evaluated for resistivity and heat resistance. The results are shown in Table 1.

Comparative Example 2-1

(1) Synthesis of Sulfonated Polymer RA

A three-necked flask equipped with a condenser tube and a three-way cock was charged with 185.3 g (540 mmol) of 2,5-dichloro-4'-phenoxybenzophenone, 15.1 g (60 mmol) of 4,4'-dichlorobenzophenone, 11.7 g (78 mmol) of sodium iodide, 11.8 g (18 mmol) of bis(triphenylphosphine) nickel dichloride, 63.0 g (240 mmol) of triphenylphosphine and 94.1 g (1.44 mol) of zinc. The flask was placed in an oil bath at 70° C. and was purged with nitrogen. Under the nitrogen atmosphere, 1000 ml of N-methyl-2-pyrrolidone was added, and the reaction was initiated. After 20 hours, the system was diluted with 500 ml of N-methyl-2-pyrrolidone. The polymerization liquid was poured into a 1:10 (by weight) hydrochloric acid/methanol solution, and the polymer was precipitated. The polymer was washed, filtered and vacuum dried to give white powder. The powder weighed 153 g. The weight-average molecular weight was 159,000. To 150 g of the polymer, 1500 ml of concentrated sulfuric acid was added. The mixture was stirred at room temperature for 24 hours for sulfonation. After the reaction, the reaction liquid was poured into a large quantity of purified water, and the sulfonated polymer was precipitated. The polymer was washed with purified water until pH 7 was reached. The sulfonated polymer was filtered, collected and vacuum dried at 90° C. The sulfonated polymer weighed 179 g. The polymer had an ion exchange capacity of 2.3 meq/g, and a weight-average molecular weight of 183,000. The polymer is represented by Structural formula (E). This polymer having sulfonic acid groups will be referred to as the polymer RA.

Structural Formula E

Polymer RA

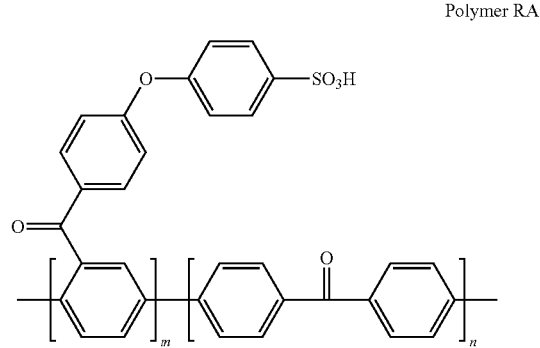

membrane was immersed in a large quantity of distilled water. This dilution removed residual NMP in the membrane. An objective membrane having a thickness of 40 µm was thus obtained. The membrane was evaluated for resistivity and heat resistance. The results are shown in Table 1.

Comparative Example 2-2

(1) Synthesis of Sulfonated Polymer RB

A 1-L three-necked flask equipped with a stirrer, a thermometer and a nitrogen inlet tube was charged with 141.5 g (337 mmol) of neopentyl 3-(2,5-dichlorobenzoyl)benzenesulfonate, 48.5 g (4.6 mmol) of the hydrophobic units B (Mn: 10,500) obtained in [Example 2-2 (1)], 6.71 g (10.3 mmol) of bis(triphenylphosphine)nickel dichloride, 1.54 g (10.3 mmol) of sodium iodide, 35.9 g (137 mmol) of triphenylphosphine and 53.7 g (821 mmol) of zinc. The flask was purged with dry nitrogen. To the flask, 430 mL of N,N-dimethylacetamide (DMAc) was added. The system was stirred for 3 hours while the reaction temperature was maintained at 80° C. The reaction liquid was diluted with 730 mL of DMAc, and insolubles were filtered.

The solution obtained was introduced into a 2-L three-necked flask equipped with a stirrer, a thermometer and a nitrogen inlet tube. The solution was heated to 115° C. with stirring, and 44 g (506 mmol) of lithium bromide was added. The mixture was stirred for 7 hours and was poured into 5 L of acetone, and the product was precipitated. The product was sequentially washed with 1N hydrochloric acid and with purified water, and was dried. As a result, an objective sulfonated polymer weighing 124 g was obtained. The weight-average molecular weight (Mw) of the polymer was 170,000. The sulfonated polymer was assumed to be represented as follows. The polymer had an ion exchange capacity of 2.3 meq/g. This polymer having sulfonic acid groups is represented by Structural formula F. This polymer will be referred to as the polymer RB.

Structural Formula F

Polymer RB

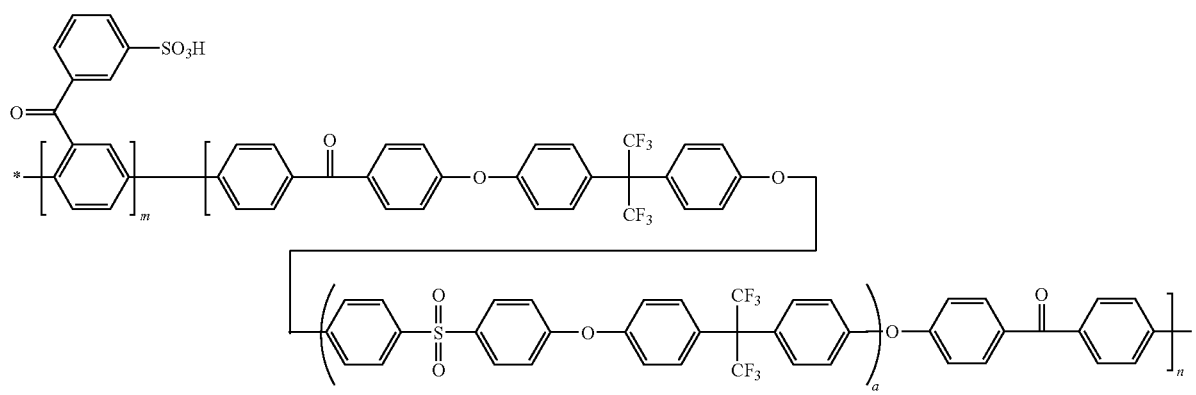

(2) Evaluation of Properties of Sulfonated Polymer RA

The sulfonated polymer RA was dissolved in a mixture of methanol/NMP=50/50 to a concentration of 15 wt %. The thus-prepared varnish was cast to give a membrane. The (2) Evaluation of Properties of Sulfonated Polymer RB The sulfonated polymer RB was dissolved in a mixture of methanol/NMP=50/50 to a concentration of 15 wt %. The thus-prepared varnish was cast to give a membrane. The membrane was immersed in a large quantity of distilled water. This dilution removed residual NMP in the membrane. An objective membrane having a thickness of 40 μm was thus obtained. The membrane was evaluated for resistivity and heat resistance. The results are shown in Table 1.

Comparative Example 2-3

(1) Synthesis of Sulfonated Polymer RC

Under a nitrogen atmosphere, 100 mL of dried N,N-dimethylacetamide (DMAc) was added to a mixture consisting of 27.18 g (38.5 mmol) of the compound monomer C represented by Structural formula C-2, 16.58 g (1.48 mmol) of the hydrophobic units synthesized in [Example 2-3 (1)], 0.79 g (1.2 mmol) of bis(triphenylphosphine)nickel dichloride, 4.20 g (16.0 mmol) of triphenylphosphine, 0.18 g (1.20 mmol) of sodium iodide and 6.28 g (96.1 mmol) of zinc.

The reaction system was heated (finally to 79° C.) with stirring, and reaction was performed for 3 hours. During the reaction, the viscosity of the system increased. The polymerization solution was diluted with 425 mL of DMAc, was stirred for 30 minutes and was filtered with use of Celite as a filter aid.

Part of the filtrate was poured into methanol, and the product was precipitated. The product was a copolymer comprising a sulfonic acid derivative protected with a neopentyl group. The copolymer had Mn of 59,400 and Mw of 178,300 as measured by GPC.

The filtrate was concentrated to 344 g with an evaporator and was combined with 10.0 g (0.116 mol) of lithium bromide. Reaction was performed at an internal temperature of 110° C. for 7 hours under a nitrogen atmosphere. After the reaction, the reaction liquid was cooled to room temperature and was poured into 4 L of acetone, and the product was precipitated. The product was filtered and was air dried. The product was then crushed with a mixer and was washed with 1500 mL of 1N hydrochloric acid with stirring. The product was filtered and was washed with ion exchange water until the washings had a pH of not less than 5. The product was dried at 80° C. overnight to give 23.0 g of an objective sulfonated polymer. This deprotected sulfonated polymer had Mn of 65,500 and Mw of 197,000. The polymer had an ion exchange capacity of 2.0 meq/g. The thus-obtained polymer RC having sulfonic acid groups is represented by Structural formula G.
Structural Formula G (2) Evaluation of Properties of Sulfonated Polymer RC The sulfonated polymer RC was dissolved in a mixture of methanol/NMP=50/50 to a concentration of 15 wt %. The thus-prepared varnish was cast to give a membrane. The membrane was immersed in a large quantity of distilled water. This dilution removed residual NMP in the membrane. An objective membrane having a thickness of 40 μm was thus obtained. The membrane was evaluated for resistivity and heat resistance. The results are shown in Table 1.

Comparative Example 2-4

(1) Synthesis of Sulfonated Polymer RD

A 1-L three-necked flask equipped with a stirrer, a thermometer and a nitrogen inlet tube was charged with 134.6 g (336 mmol) of neopentyl 3-(2,5-dichlorobenzoyl)benzenesulfonate, 47.4 g (6.5 mmol) of the hydrophobic units D synthesized in [Example 2-4 (1)], 6.71 g (10.3 mmol) of bis(triphenylphosphine)nickel dichloride, 35.9 g (136 mmol) of triphenylphosphine, 1.54 g (10.3 mmol) of sodium iodide and 53.7 g (820 mmol) of zinc. Under a nitrogen atmosphere, 430 mL of dried N,N-dimethylacetamide (DMAc) was added to the flask.

The reaction system was heated (finally to 79° C.) with stirring, and reaction was performed for 3 hours. During the reaction, the viscosity of the system increased. The polymerization solution was diluted with 730 mL of DMAc, was stirred for 30 minutes and was filtered with use of Celite as a filter aid.

Part of the filtrate was poured into methanol, and the product was precipitated. The product was a copolymer comprising a sulfonic acid derivative protected with a neopentyl group. The copolymer had Mn of 59,400 and Mw of 138,000 as measured by GPC.

The filtrate was concentrated with an evaporator and was combined with 44.0 g (506 mmol) of lithium bromide. Reaction was performed at an internal temperature of 110° C. for 7 hours under a nitrogen atmosphere. After the reaction, the reaction liquid was cooled to room temperature and was poured into 5 L of acetone, and the product was precipitated. The product was filtered and was air dried. The product was then crushed with a mixer and was washed with 1N hydrochloric acid with stirring. The product was filtered and was Polymer RC

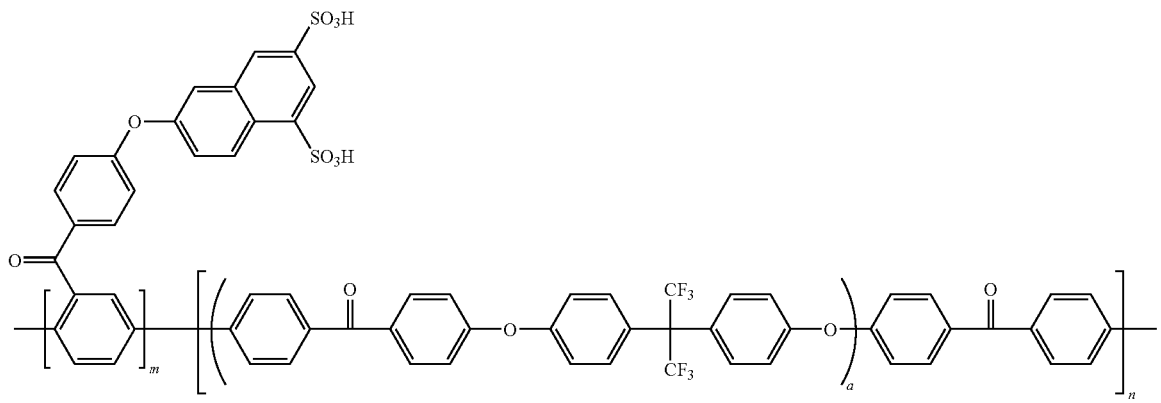

washed with ion exchange water until the washings had a pH of not less than 5. The product was dried at 80° C. overnight to give 122 g of an objective sulfonated polymer. This deprotected sulfonated polymer had Mn of 68,000 and Mw of 140,000. The polymer had an ion exchange capacity of 2.4 meq/g. The thus-obtained polymer RD having sulfonic acid groups is represented by Structural formula H.

Structural Formula H

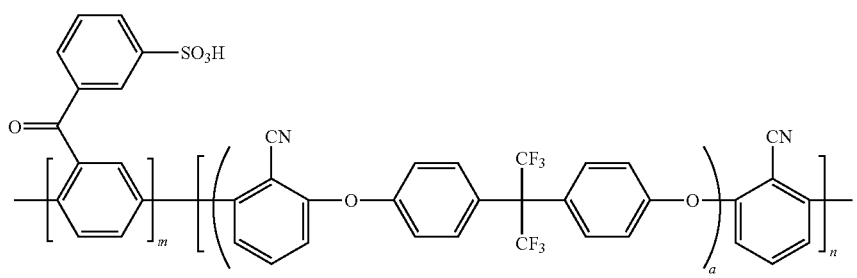

Polymer RD

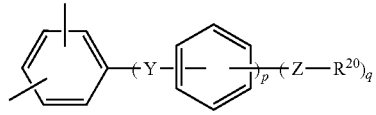

(C)

(2) Evaluation of Properties of Sulfonated Polymer RD

The sulfonated polymer RD was dissolved in a mixture of methanol/NMP=50/50 to a concentration of 15 wt %. The thus-prepared varnish was cast to give a membrane. The membrane was immersed in a large quantity of distilled water. This dilution removed residual NMP in the membrane. An objective membrane having a thickness of 40 μm was thus obtained. The membrane was evaluated for resistivity and heat resistance. The results are shown in Table 1.

TABLE 1

| Sulfonated polymer | Nitrogen-containing heterocyclic aromatic group (—Ar) | Resistivity (Ω·cm) | Heat resistance 160° C. × 24 h Insoluble content (wt %) |
|---|---|---|---|
| Ex. 2-1 | Polymer A-N1 | Pyrrole | 3.6 | 0 |
| Ex. 2-2 | Polymer B-N1 | Imidazole | 3.0 | 0 |
| Ex. 2-3 | Polymer C-N1 | Benzothiazole | 3.0 | 0 |
| Ex. 2-4 | Polymer D-N1 | Imidazole | 2.7 | 0 |
| Comp. Ex. 2-1 | Polymer RA | — | 3.6 | 80 |
| Comp. Ex. 2-2 | Polymer RB | — | 3.1 | 35 |
| Comp. Ex. 2-3 | Polymer RC | — | 3.0 | 15 |
| Comp. Ex. 2-4 | Polymer RD | — | 2.6 | 20 |

The results in Table 1 proved that the polymers having the nitrogen-containing heterocyclic aromatic groups had high proton conductivity and high heat resistance.

The invention claimed is:

1. A polymer comprising a main chain comprising a polyphenylene structure, and a structure comprising a side chain having a sulfonic acid group and a side chain having a nitrogen-containing heterocyclic group, and including a repeating structural unit represented by Formula (C) as the structure comprising a side chain having a nitrogen-containing heterocyclic group:

wherein Z is at least one structure selected from the group consisting of a direct bond, —O— and —S—; Y is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; R$^{20}$ is a nitrogen-containing heterocyclic group; q is an integer of 1 to 5; and p is an integer of 0 to 4.

2. The polymer according to claim 1, wherein the side chain having a nitrogen-containing heterocyclic group is represented by Formula (D):

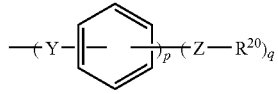

(D)

wherein Z is at least one structure selected from the group consisting of a direct bond, —O— and —S—; Y is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; R$^{20}$ is a nitrogen-containing heterocyclic group; q is an integer of 1 to 5; and p is an integer of 0 to 4.

3. The polymer according to claim 1 or 2, wherein the nitrogen-containing heterocyclic group is at least one group derived from a compound selected from the group consisting of nitrogen-containing heterocyclic compounds and derivatives thereof selected from pyrrole, thiazole, isothiazole, oxazole, isoxazole, pyridine, imidazole, imidazoline, pyrazole, 1,3,5-triazine, pyrimidine, pyridazine, pyrazine, indole, quinoline, isoquinoline, purine, benzimidazole, benzoxazole, benzthiazole, tetrazole, tetrazine, triazole, carbazole, acridine, quinoxaline, quinazoline and derivatives of these compounds.

4. The polymer according to claim 1, wherein the side chain having a sulfonic acid group is represented by Formula (E):

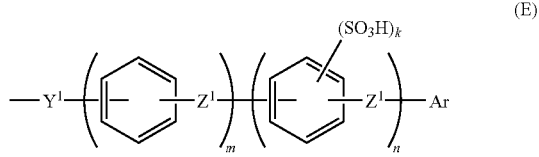

(E)

wherein $Y^1$ is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; $Z^1$ is at least one structure selected from the group consisting of a direct bond, —(CH$_2$)$_l$— (wherein l is an integer of 1 to 10), —C(CH$_3$)$_2$—, —O— and —S—; Ar is an aromatic group having a substituent represented by —SO$_3$H, —O(CH$_2$)$_h$SO$_3$H or —O(CF$_2$)$_h$SO$_3$H (wherein h is an integer of 1 to 12);

m is an integer of 0 to 10; n is an integer of 0 to 10; and k is an integer of 1 to 4.

5. The polymer according to claim 1, wherein the polymer includes a repeating structural unit represented by said Formula (C) and a repeating unit represented by Formula (A):

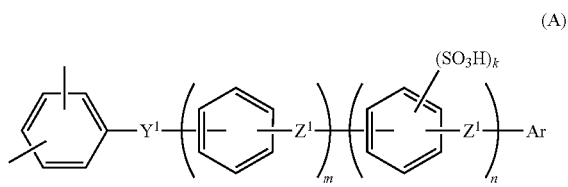

(A)

wherein $Y^1$ is at least one structure selected from the group consisting of —CO—, —SO$_2$—, —SO—, —CONH—, —COO—, —(CF$_2$)$_l$— (wherein l is an integer of 1 to 10) and —C(CF$_3$)$_2$—; $Z^1$ is at least one structure selected from the group consisting of a direct bond, —(CH$_2$)$_l$— (wherein l is an integer of 1 to 10), —C(CH$_3$)$_2$—, —O— and —S—; Ar is an aromatic group having a substituent represented by —SO$_3$H, —O(CH$_2$)$_h$SO$_3$H or —O(CF$_2$)$_h$SO$_3$H (wherein h is an integer of 1 to 12); m is an integer of 0 to 10; n is an integer of 0 to 10; and k is an integer of 1 to 4.

6. The polymer according to claim 5, wherein the polymer further includes a structure represented by Formula (B):

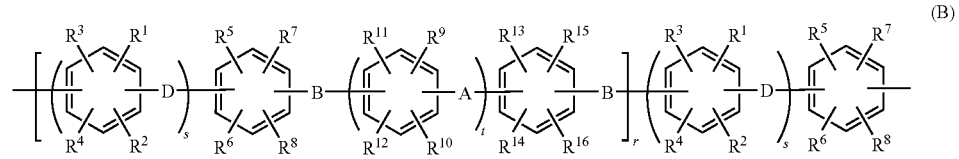

(B)

wherein A and D are each at least one structure selected from the group consisting of a direct bond, —CO—, —SO$_2$—, —SO—, —CONH—, —(CF$_2$)$_l$— (wherein l is an integer of 1 to 10), —(CH$_2$)$_l$- (wherein l is an integer of 1 to 10), —CR'$_2$— (wherein R' is an aliphatic hydrocarbon group, an aromatic hydrocarbon group or a halogenated hydrocarbon group), a cyclohexylidene group, a fluorenylidene group, —O— and —S—; Bs are each an oxygen atom or a sulfur atom; $R^1$ to $R^{16}$ are the same or different from one another and are each at least one atom or group selected from the group consisting of a hydrogen atom, a fluorine atom, alkyl groups, partially or completely halogenated alkyl groups, allyl groups, aryl groups, nitro group and nitrile group; s and t are each an integer of 0 to 4; and r is an integer of 0 or 1 or greater.

7. A proton conductive membrane comprising the polymer according to claim 1.

8. A proton conductive membrane comprising the polymer according to claim 2.

9. A proton conductive membrane comprising the polymer according to claim 3.

10. A proton conductive membrane comprising the polymer according to claim 4.

11. A proton conductive membrane comprising the polymer according to claim 5.

12. A proton conductive membrane comprising the polymer according to claim 6.

13. The polymer according to claim 1, which comprises a polyphenylene block moiety whose phenylene units each comprise the side chain having a sulfonic acid group, and a polyphenylene block moiety whose phenylene units each comprise the side chain having a nitrogen-containing heterocyclic group.

14. The polymer according to claim 2, which comprises a polyphenylene block moiety whose phenylene units each comprise the side chain having a sulfonic acid group, and a polyphenylene block moiety whose phenylene units each comprise the side chain having a nitrogen-containing heterocyclic group.

15. The polymer according to claim 4, which comprises a polyphenylene block moiety whose phenylene units each comprise the side chain having a sulfonic acid group, and a polyphenylene block moiety whose phenylene units each comprise the side chain having a nitrogen-containing heterocyclic group.

16. The polymer according to claim 4, wherein the side chain having a sulfonic acid group and the side chain having a nitrogen-containing heterocyclic group are bonded to different phenylene units.

* * * * *